(12) United States Patent
Carlisle et al.

(10) Patent No.: US 7,503,903 B2
(45) Date of Patent: Mar. 17, 2009

(54) AUTOMATED FLUID FLOW CONTROL SYSTEM

(75) Inventors: Jeffrey Alan Carlisle, Stratham, NH (US); Lawrence Michael Kuba, Nashua, NH (US)

(73) Assignee: Fluidnet Corporation, Portsmouth, NH (US)

( * ) Notice: Subject to any disclaimer, the term of this patent is extended or adjusted under 35 U.S.C. 154(b) by 605 days.

(21) Appl. No.: 11/062,391

(22) Filed: Feb. 22, 2005

(65) Prior Publication Data

US 2006/0004330 A1 Jan. 5, 2006

Related U.S. Application Data

(60) Provisional application No. 60/608,956, filed on Feb. 20, 2004.

(51) Int. Cl.
*A61M 31/00* (2006.01)
*A61M 5/00* (2006.01)

(52) U.S. Cl. .............................. 604/67; 604/65; 604/246

(58) Field of Classification Search .................. 604/80, 604/81, 253, 65, 67; 60/545; 91/527; 137/315.03, 137/599.07

See application file for complete search history.

(56) References Cited

U.S. PATENT DOCUMENTS

| 3,934,473 A | * | 1/1976 | Griffo | ...................... 73/861.84 |
| 4,489,616 A | * | 12/1984 | Priddy | ...................... 73/861.79 |
| 4,533,347 A | * | 8/1985 | Deckert | ........................ 604/81 |
| 4,876,492 A | * | 10/1989 | Lester et al. | ................. 318/254 |

* cited by examiner

*Primary Examiner*—Nicholas D Lucchesi
*Assistant Examiner*—Aarti Bhatia
(74) *Attorney, Agent, or Firm*—McLane, Graf, Raulerson & Middleton, P.A.; Scott C. Rand

(57) ABSTRACT

A device for control of fluid flow with closed loop quasi static adjustment of in-line pressure-based resistance. The disclosed device and methods of using the device provide for the ability to control a flow rate with a highly portable device; the ability for an operator to safely use the device with minimal training; the ability to automatically switch between a primary and secondary fluid; the ability to maintain a flow rate through a tubing set even when the control device is removed; and the ability to measure fluids introduced with a manual bolus injection.

20 Claims, 30 Drawing Sheets

Fig 6
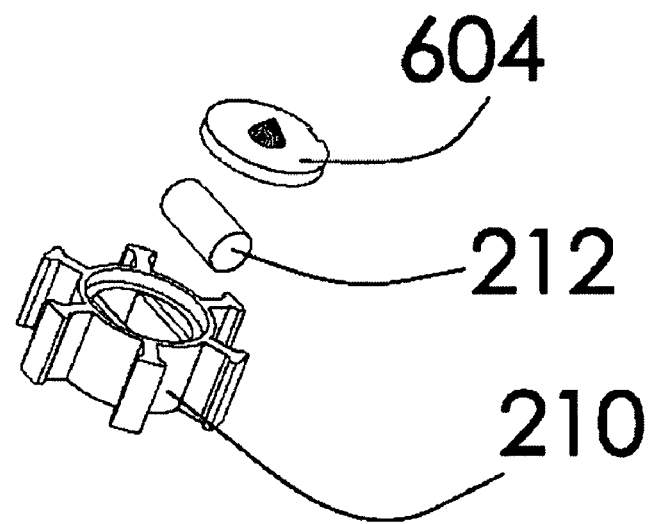

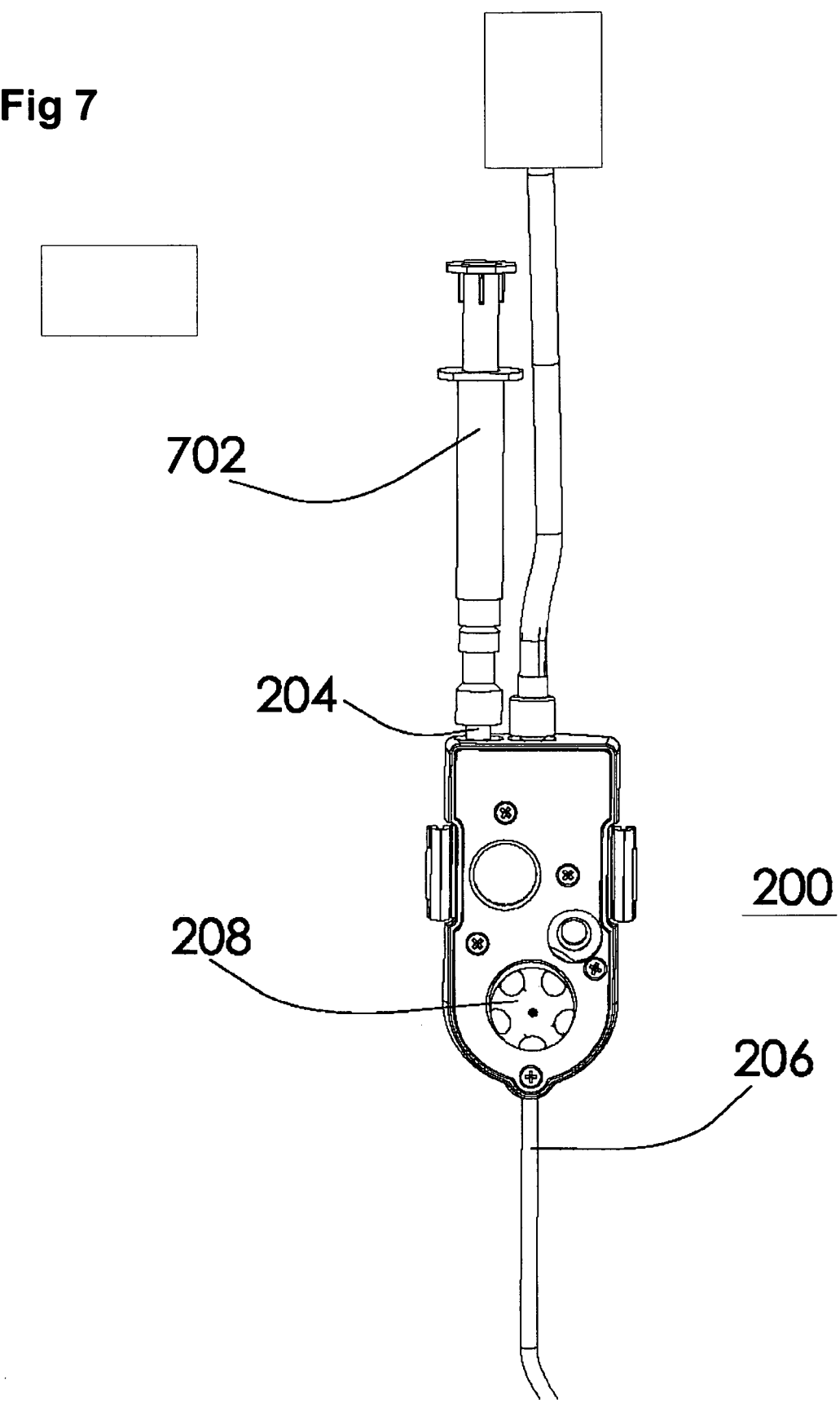

AUTOMATED FLUID FLOW CONTROL SYSTEM

RELATED APPLICATIONS

This application claims priority to U.S. Provisional Patent Application Ser. No. 60/608,956, filed on Feb. 20, 2004, which was converted from U.S. patent application Ser. No. 10/783,042 filed on Feb. 20, 2004 under 37 CFR 1.53(c)(2).

FIELD OF THE INVENTION

The present invention relates to intravenous infusion therapy. More specifically, the invention relates to a system, components of the system and methods associated with the system for organizing the fluid flow for applications which require an accommodation of a broad flow rate range, a wide range of input and output pressures, and a wide range of delivered fluid viscosities, such as those seen with Intravenous (IV) infusion therapy.

BACKGROUND

Conventionally, healthcare providers have had three technical options for the intravenous infusions. Many intravenous infusions are controlled by manually adjusting a resistance in the flow path between a fluid source and the patient, based on the operator's observation of the rate of drips formed within a chamber in line with the fluid flow. The flow rate range that can be controlled with this method is limited by the relatively large and fixed size of the drops and the relatively low reliability of the human operator to accurately compute the flow rate. This method is critically flawed by virtue of the fact that it requires a human observer to maintain an accurate and consistent flow rate. In many circumstances, a trained human observer is not available. This manual method also lacks an important ability to electronically record and communicate the results of the infusion.

A relatively small number of infusions are controlled with the use of a fixed volume of liquid under a fixed amount of pressure and a fixed resistance, providing a fixed flow rate. Unfortunately, the fixed rate and fixed fluid volume do not provide the flexibility required for most infusions. Similar to a manual infusion, this method does not provide the opportunity to electronically record the results of the infusion.

Because of the strong requirement for more precise control of flow rate, flexibility of fluid volumes, and the desire to keep track of the flow information, many infusions are controlled using a positive displacement fluid pump. These large fluid volume positive displacement devices are generally of the peristaltic or reciprocating piston type. Both types come at a price of complexity, size, weight, limited battery life, and significant financial cost. Early versions of positive displacement pumps created a new hazard for patients in what was known as "runaway infusion," where the highly controlled fluid flow was suddenly uncontrolled when a door or other containment mechanism on the pump was released. In response to this undesirable feature, pumps were later required to incorporate "flow stop" mechanisms, so that the flow rate would stop entirely if the fluid tubing were removed form the flow control device. Unfortunately, the cessation of flow is sometimes as hazardous to patients as a sudden increase. Another unintended consequence of positive pumping systems is the possibility of infusing lethal amounts of air into a patient. This possibility did not exist with low pressure gravity infusions. As a result, positive displacement pumps have incorporated air detection systems to prevent this hazard, yet these alarm systems are the source of very significant nuisance alarms, resulting in operator inefficiency and patient anxiety.

The present invention recognizes that most intravenous infusions require only moderate infusion and that portability and simplicity should not be compromised for any infusion.

SUMMARY OF THE INVENTION

Intravenous infusions can be broken into two broad categories: infusions where the flow rates are relatively high with relatively low requirements for absolute flow accuracy, and infusions that must be made with maximal precision and flow continuity. The later classification includes those drugs which have powerful effects upon the cardiovascular system or powerful anesthetics. This invention covers the former classification which includes fluids for hydration, electrolytes, nutrients, antibiotics. These fluids and medications do not require great precision and comprise the overwhelming majority of infusions required for patients.

The invention is directed to fluid administration apparatus and a method for using this apparatus, comprising a fluid pathway assembly and a flow control device wherein fluid flowing through the fluid flow system is controlled via closed loop quasi-static adjustment of in-line pressure-based resistance.

The above and other features of the invention, including various novel details of construction and combinations of parts, will now be more particularly described with reference to the accompanying drawings and pointed out in the claims. It will be understood that the particular device embodying the invention is shown by way of illustration only and not as a limitation of the invention. The principles and features of this invention may be employed in various and numerous embodiments without departing from the scope of the invention.

BRIEF DESCRIPTION OF THE FIGURES

These and other features, aspects, and advantages of the apparatus and methods of the present invention will become better understood with regard to the following description, appended claims, and accompanying drawings where:

FIG. 5b shows the collapsed view of FIG. 5a.

FIG. 6 details the impeller and magnet assembly components of FIG. 2;

FIG. 7 shows the cassette of 6 with a syringe on the secondary input;

DETAILED DESCRIPTION

Figure 1A:
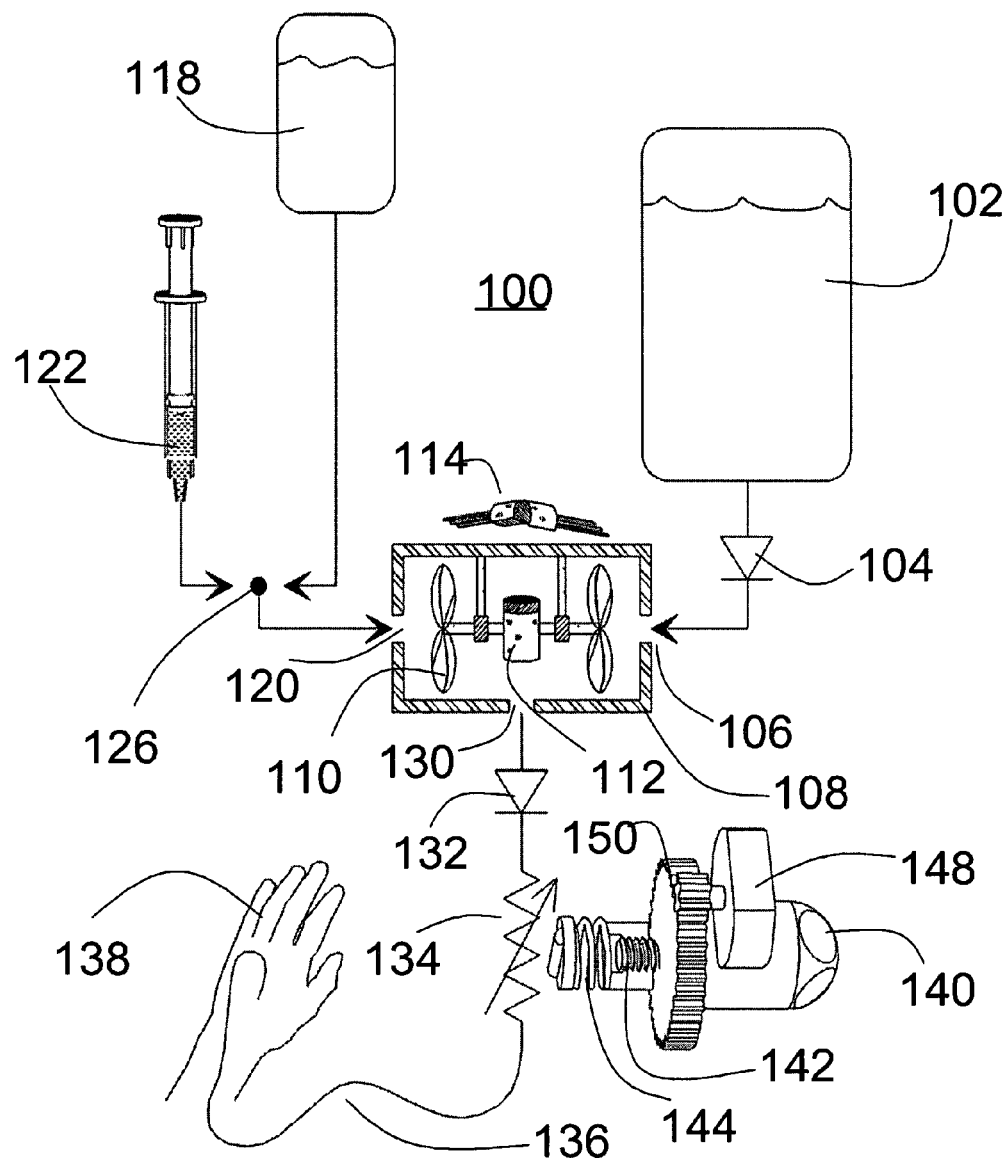
FIG. 1a is a schematic representation of the fluid administration system in accordance with the present invention.

The essential components of the invention are described with reference to FIG. 1a. A medical fluid administration system 100 includes one or more sources of fluid, one or more one-way check valves, a bi-directional flow measurement device, and a variable fluid resistance, modulated manually, or by servomechanism, or both, all of which are described in detail herein.

Primary fluid source 102 is represented schematically as a large-volume bag. The content of primary fluid source 102 flows via primary check valve 104 and into primary input 106 to an impeller housing 108. The movement of fluid causes impeller 110 to turn in a given direction based on the geometry of impeller 110. In one embodiment of the present invention, impeller 110 is connected to permanent magnet 112, causing permanent magnet 112 to turn as impeller 110 turns. Electromagnet coils 114 may be used as a sensor to detect movement of permanent magnet 112. It is contemplated that other embodiments in accordance with the present invention will utilize a non-metallic impeller without detracting from the present invention.

Fluid exits impeller housing 108 via outlet channel 130 through an outlet tube 136 and travels via output check valve 132 to variable resistance 134, indicated schematically by a variable resistor. In practice, variable resistance 134 may optionally be realized as a variably pinched tube element (illustrated in FIG. 4 as pinch bar 414). The function of output check valve 132 may be controlled by a separate check valve or by the natural tendency of the variable resistance 134, if tube 136 collapses and closes off flow in response to reduced or negative pressure from outlet channel 130. A manual control, indicated as manual control knob 140, regulates variable resistance 134, for example, using a threaded shaft 142 that compresses a spring 144, exerting a controlled variable force between spring 144 and outlet tube 136 as manual control knob 140 is turned. A gear motor 148 and gear 150 turn the same threaded shaft 142 as the manual control knob 140, providing mechanized regulation of the same variable resistance 134. The regulated fluid flow emerging from variable resistance 134 travels via outlet tube 136 into its final destination, shown as patient 138.

A secondary fluid source could include secondary fluid source 118 or injectable fluid reservoir 122. The optional connections of secondary fluid source 118 or injectable fluid reservoir 122 feed into fluid administration system 100 as indicated by the directional arrows leading from secondary fluid source 118 and injectable fluid reservoir 122 and join at secondary fluid input node 126. The selected secondary fluid source, either secondary fluid source 118 or injectable fluid reservoir 122, flows from secondary fluid input node 126 to secondary input 120 into impeller housing 108. Fluid flow arising from secondary input to impeller housing 120 and exiting from outlet channel 130 of impeller housing 108 will tend to move impeller 110. Given the proper geometry of impeller 110, the movement of impeller 110 and permanent magnet 112 will be the opposite of that when fluid flows through primary input 106 to impeller housing 108. Electromagnet coils 114 can measure both the speed and direction of permanent magnet 112 as it rotates.

Due to the symmetry of electromagnetism, electromagnet coils 114 may be used as a sensor or as an electromagnetic driver, in the same way that a loudspeaker may also be used as a microphone. It is possible, then, to use electromagnet coils 114 to apply a torque to permanent magnet 112, so that it tends to align with the magnetic field created by electromagnet coils 114. The magnetic field created by electromagnet coils 114 can be static or time variant.

Figure 1B:
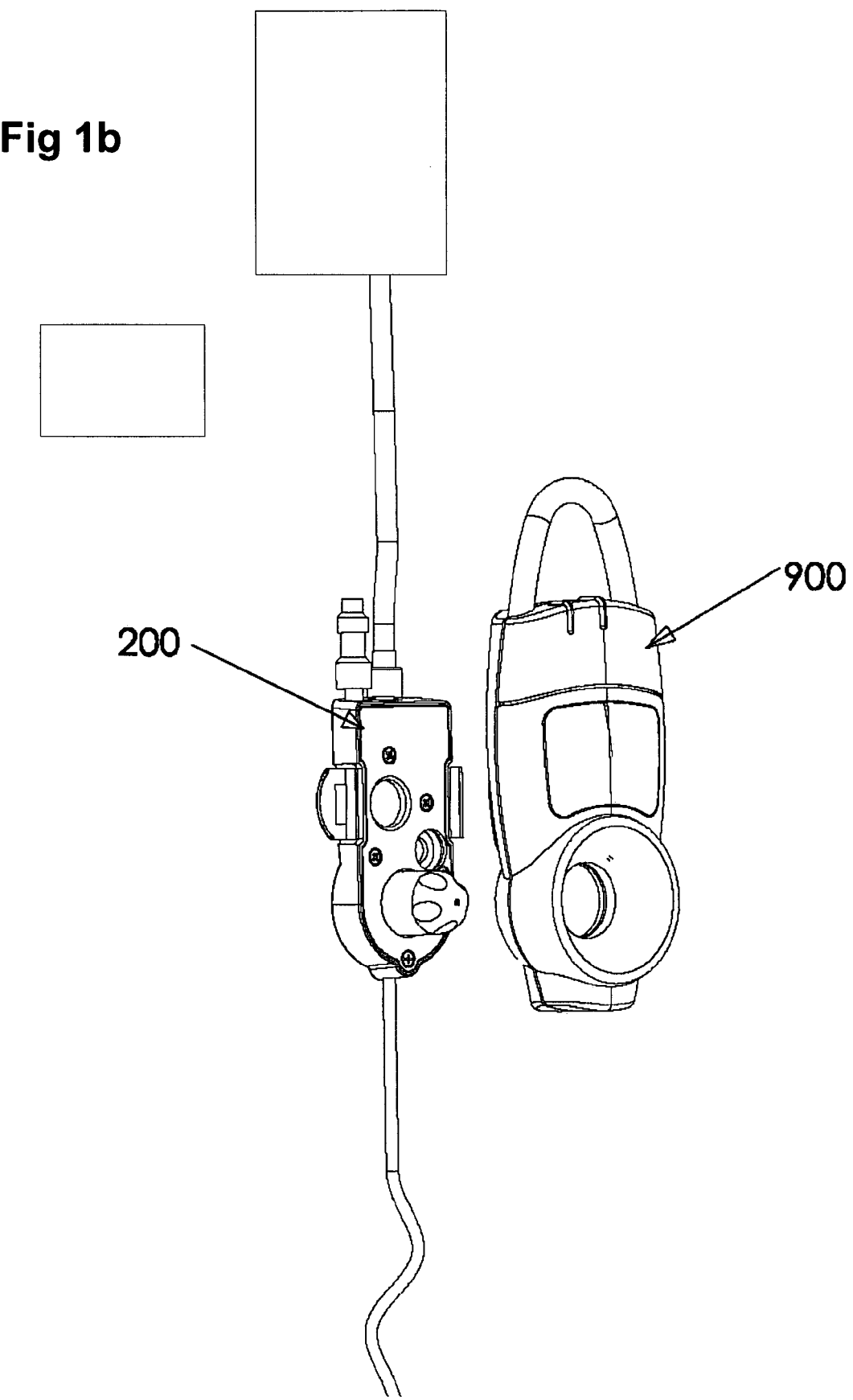
FIG. 1b shows the two major assemblies of the invention.

The components of FIG. 1a are separable into fluid sources 102, 118, 122, with associated inlet lines, fluid pathway assembly 200 (shown in FIG. 1b), flow control device 900 (shown in FIG. 1b), and patient 128. FIG. 1b shows the two major assemblies, fluid pathway assembly 200 and flow control device 900, in a separated state. Fluid sources 102, 118 and 122 may be filled with fluids for hydration, electrolytes, antibiotics, blood products, nutrient solutions, or any fluids with flow rates in excess of 10 milliliters per hour.

Figure 2:
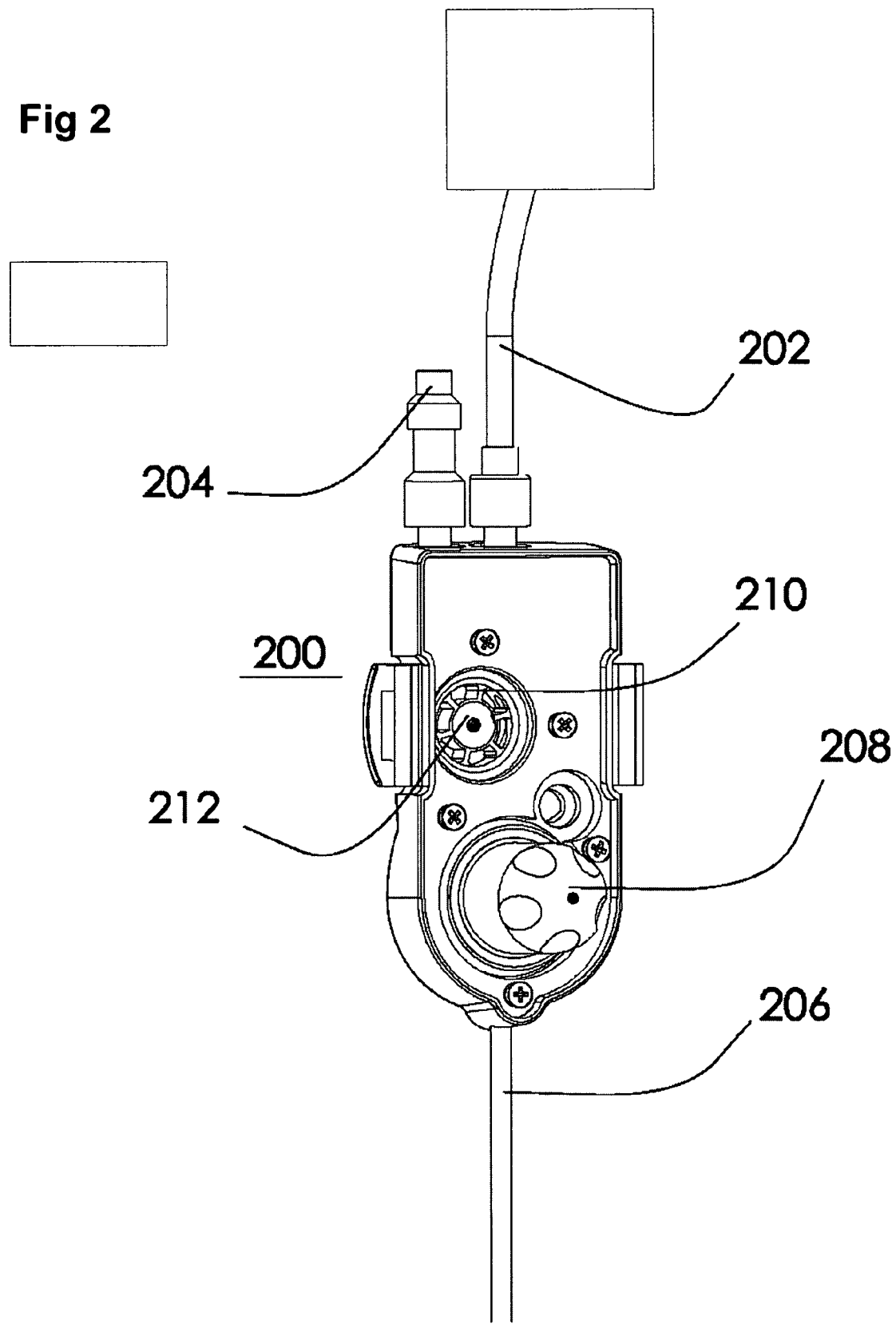
FIG. 2 is a front exterior view of a fluid administration cassette with a primary input line attached.

The major elements of fluid pathway assembly 200 are shown in FIG. 2. In its simplest operation, fluid enters fluid pathway assembly 200 via primary inlet line 202. Fluid flows through a watertight set of pathways, passing by in-line rotary flow impeller 210 and exiting to outlet tube 206 via resistance control knob 208. The use of a secondary fluid source connection receptacle 204 is demonstrated in subsequent drawings. Permanent magnet 212 is encapsulated within in-line rotary flow impeller 210, so that the movement of in-line rotary flow impeller 210 may be sensed or compelled electromagnetically. Resistance control knob 208 may be adjusted rotationally to modulate the resistance of fluid flow through fluid pathway assembly 200. Additionally, although the present embodiment has been described as having a control knob, it is to be understood that the invention is not intended to be limited to a knob, and any other kind of mechanical control known to those of ordinary skill in the art, such as slides, rollers, etc. are contemplated by the present invention.

Figure 3:
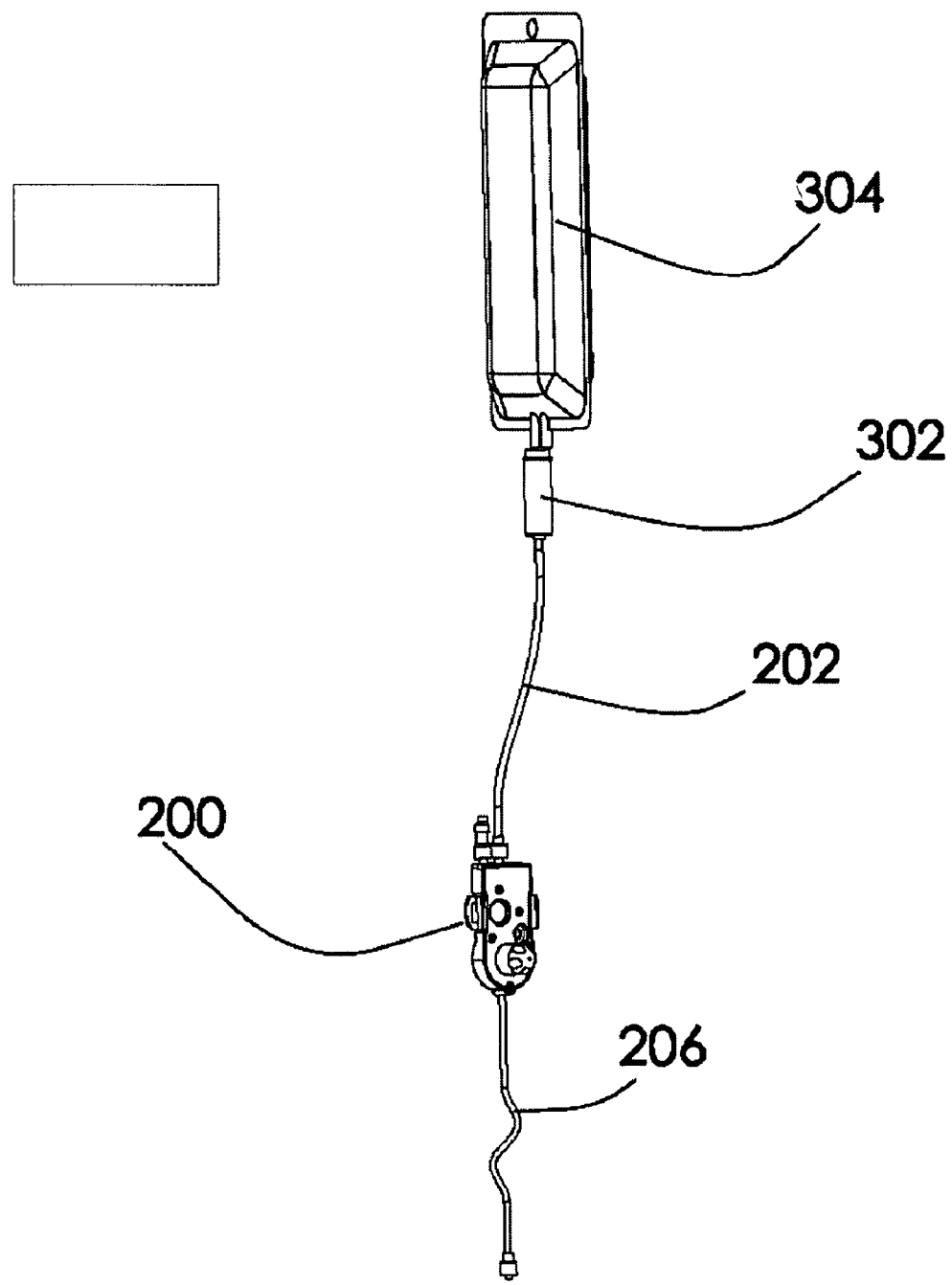
FIG. 3 shows a drop-forming chamber associated with the primary line of FIG. 2.

In FIG. 3, the relative positions of primary fluid reservoir 304 and drop forming chamber 302 are shown. In most cases, it is the positive hydrostatic pressure of primary fluid reservoir 304, relative to the position of outlet tube 206, that compels fluid to flow. A conventional drop forming chamber 302 is included for reference, but is not incorporated in the function of the invention.

Figure 4:
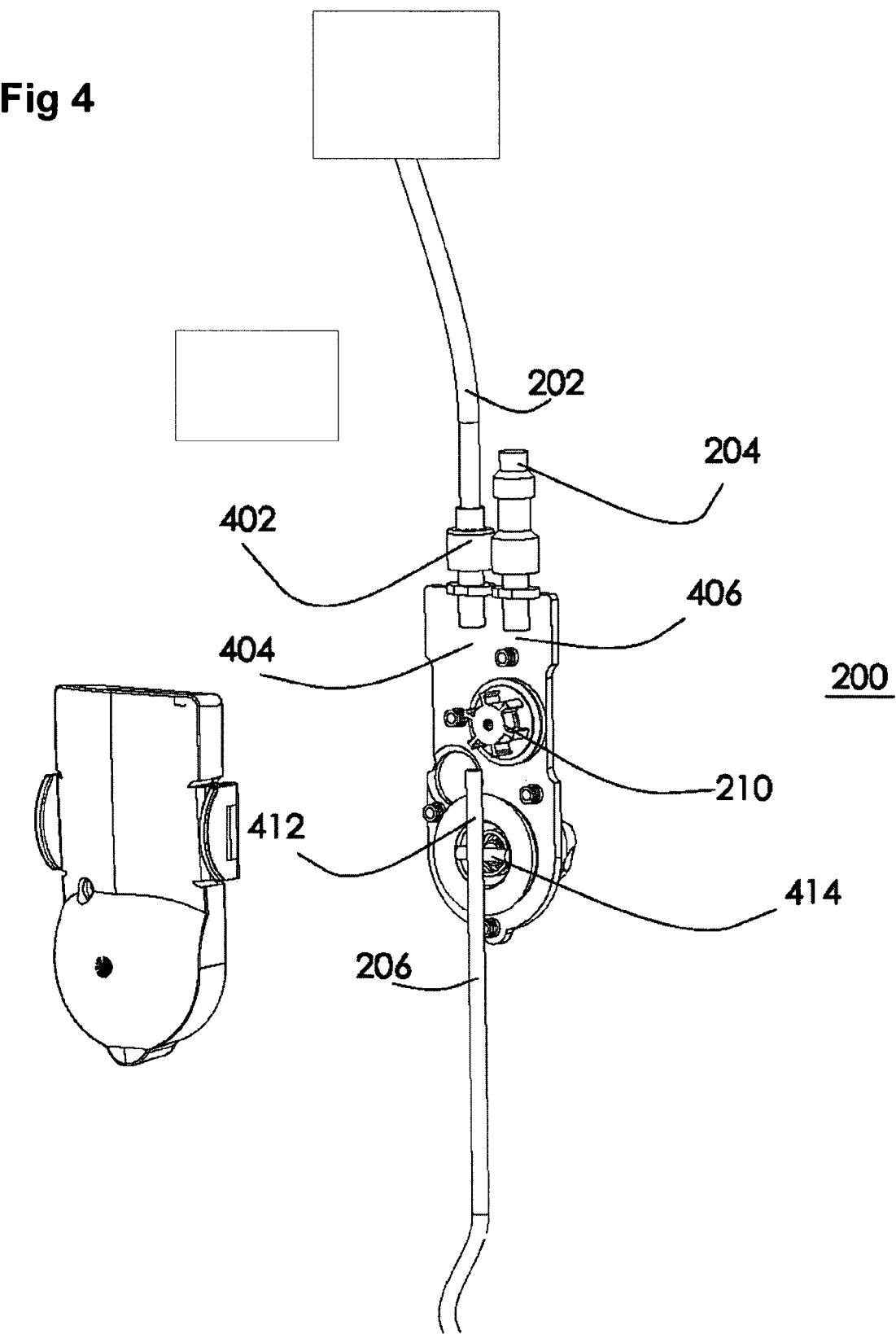
FIG. 4 shows a transparent rear view of the cassette of FIG. 2.

A reverse view of fluid pathway assembly 200, shown in FIG. 4, reveals additional functionality. Fluid entering fluid pathway assembly 200 via primary inlet line 202 passes through primary one-way valve 402 and continues into primary channel 404. The flow of this fluid will tend to rotate in-line rotary flow impeller 210 as it travels into outlet channel 412 and then outlet tube 206. A resistive element is created by the interference of resistive component or pinch bar 414 and outlet channel 412.

The hardware design and recommended usage favor situations involving little overlap of fluid flows from the two directions, as described here by way of example. If a fluid source were connected to secondary fluid source connection receptacle 204 and if said source had a pressure greater than that of primary inlet line 202, then the normal action of primary one-way valve 402 would be to close. Flow from secondary fluid source connection 204 would then travel through secondary channel 406 on its way to outlet channel 412 and then to outlet tube 206. The geometry of the pathways within fluid pathway assembly 200 are such that flow from connection receptacle for secondary fluid source 204 will tend to spin in-line rotary flow impeller 210 in the opposite direction than flow arising from primary inlet line 202.

In a typical IV therapy situation, an on-going large-volume infusion from primary inlet line 202 may be interrupted by the administration of a smaller volume of antibiotic from connection receptacle for secondary fluid source 204. Common clinical practice is to infuse an antibiotic over a relatively short period of time, so that an effective level is reached in the patient's blood stream, followed by cessation of antibiotic infusion for a relatively long period of several hours. Thus, when an antibiotic is connected to connection receptacle for secondary fluid source 204 and placed higher than primary fluid reservoir 304, the infusion automatically switches over to pure antibiotic administration, which is detected and regulated by the system. The system similarly permits a rapid bolus infusion, for example from connection receptacle for secondary fluid source 204. Again, the bolus flow forces primary one-way valve 402 to close, so in-line rotary flow impeller 210 reverses it direction and allows for the separate measurement of the bolus.

Figure 5A:
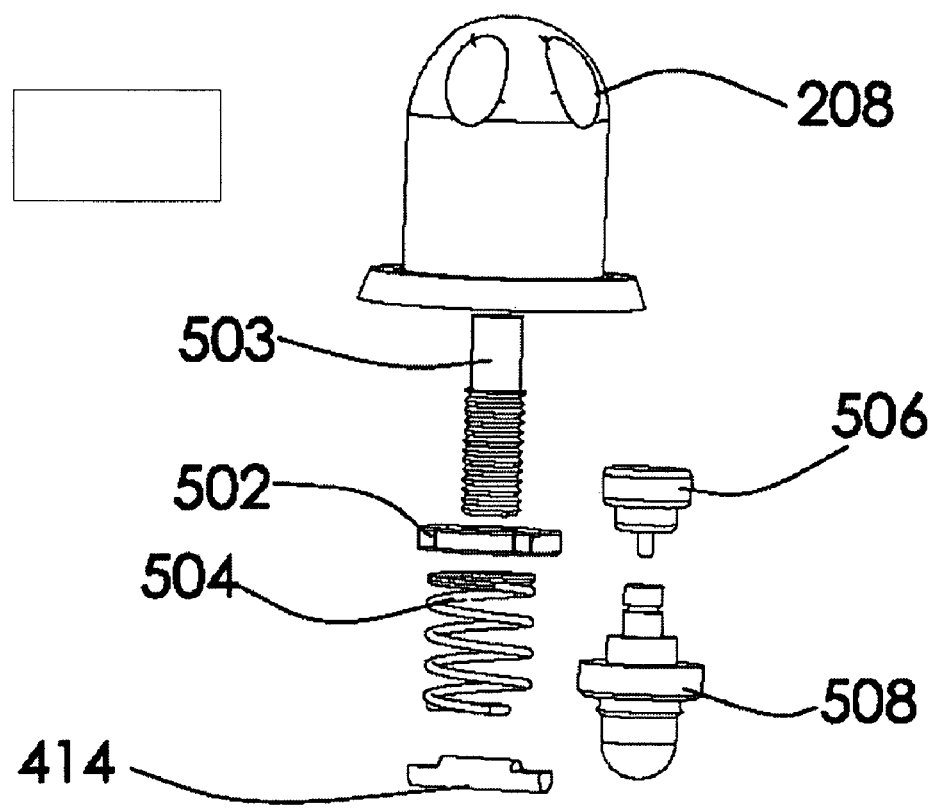
FIG. 5a shows an exploded view of the variable resistance mechanism of FIG. 2.

FIG. 5a provides an exploded view illustrating the details of the resistive elements, shown schematically as variable resistance 134 in FIG. 1a. With respect to FIG. 5a, resistance control knob 208 may be rotated manually in either clockwise or counterclockwise fashion. Threaded shaft 503 is securely attached to resistance control knob 208, following its rotation without slippage. Advancing nut 502 is threaded upon threaded shaft 503. When resistance control knob 208 turns, threaded shaft 503 will follow. If advancing nut 502 is prevented from turning, then it will, via a normal screw machine function, travel up and down threaded shaft 503, depending on the direction of the rotation. As advancing nut 502 translates up or down the length of threaded shaft 503, it interferes with occlusion spring 504 and applies more or less compression as it travels. The bottom surface of occlusion spring 504 presses upon pinch bar 414, applying a greater or lesser force to pinch bar 414. While not shown in this view, it can be understood that pinch bar 414 can be used to apply a variable force to a flexible tube. FIG. 5a further illustrates two elements that are part of flow control device 900 (previously illustrated in FIG. 1b), namely a gear adjusting motor 506 and a drive wheel 508. Drive wheel 508 may also be externally driven, as shown in FIG. 5a, by adjusting gear motor 506. While FIG. 5a illustrates a gear adjusting motor 506, it should be understood that the present invention is not limited in this respect, and other motors known to those of ordinary skill in the art are contemplated and may be used without detracting from the present invention.

Figure 5B:
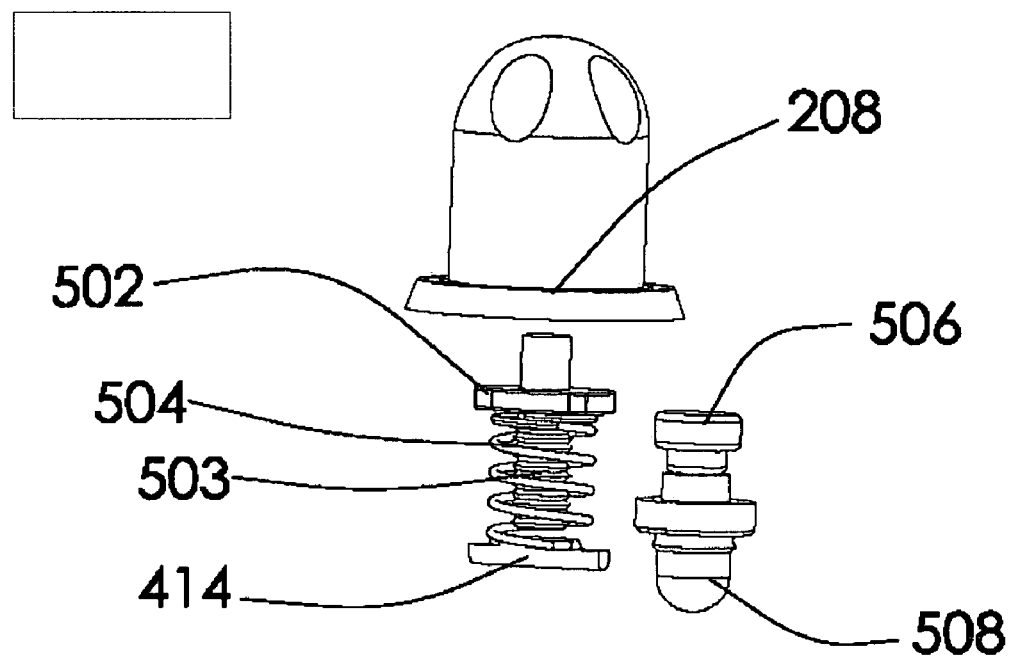

FIG. 5b illustrates the components of FIG. 5a in a functional and assembled form. The rotational position of resistance control knob 208 determines the position of advancing nut 502 upon threaded shaft 503 and therefore sets the force applied to pinch bar 414 by occlusion spring 504. The rotation of resistance control knob 208 may be by hand or by the activation of adjusting gear motor 506 which turns drive wheel 508 which, by friction, causes the rotation of resistance control knob 208.

FIG. 6 shows an exploded view of permanent magnet 212, as it is embedded within in-line rotary flow impeller 210. Magnet cover 604 provides a seal for open cavities within in-line rotary flow impeller 210, resulting in an assembly that has a specific gravity equal to that of water. Neutral buoyancy reduces the rotating friction of this impeller, making it more sensitive at low flow rates.

In another embodiment, bolus administration syringe 702 can be attached to secondary fluid source connection receptacle 204 as shown in FIG. 7 and shown schematically in FIG. 1a with injectable fluid reservoir 122. A manual bolus may be injected into connection receptacle for secondary fluid source 204, traveling through fluid pathway assembly 200 to outlet tube 206. The flow resistance established by resistance control knob 208 is easily overcome with the additional pressure applied by a manual administration from bolus administration syringe 702 (i.e., injection of the bolus by depression of the plunger on syringe 702).

Figure 8A:
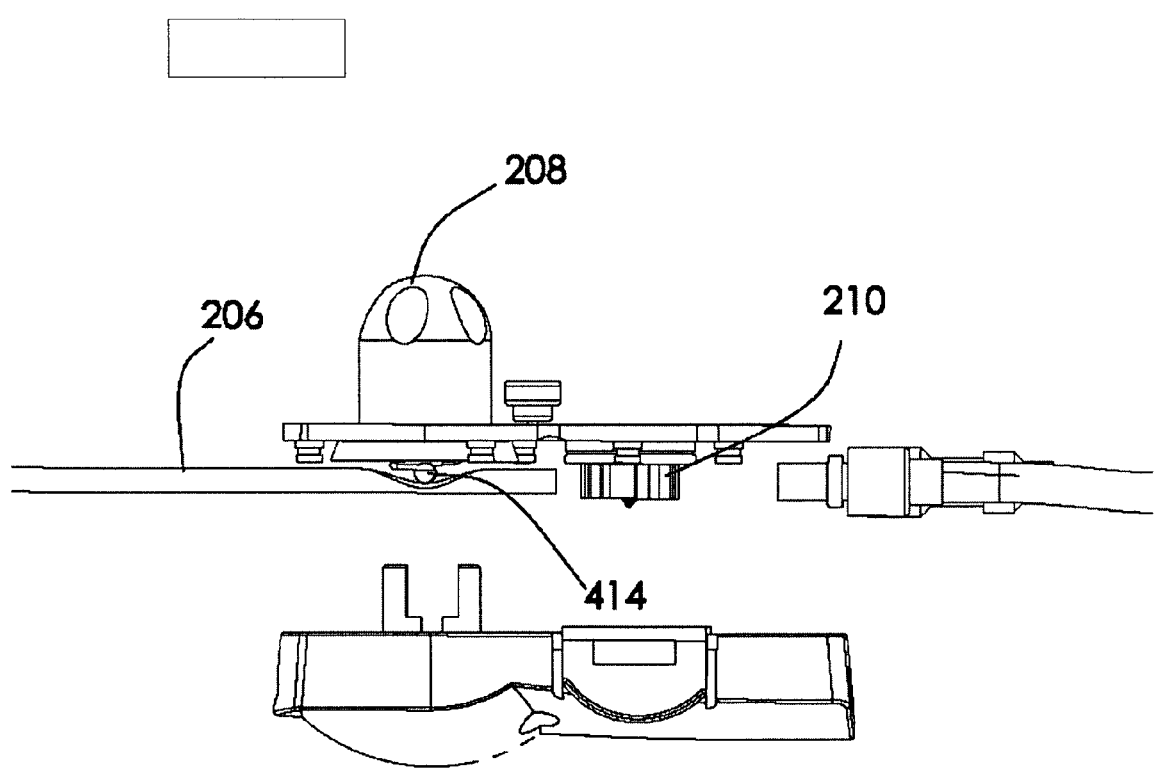
FIGS. 8a, 8b, and 8c illustrate operation of the control knob and fluid flow restriction apparatus of the cassette.

The close-up view of resistance control knob 208 in FIG. 8a shows the relationship of outlet tube 206 with pinch bar 414 when the flow has been restricted. In-line rotary flow impeller 210 is shown for reference.

Figure 8B:
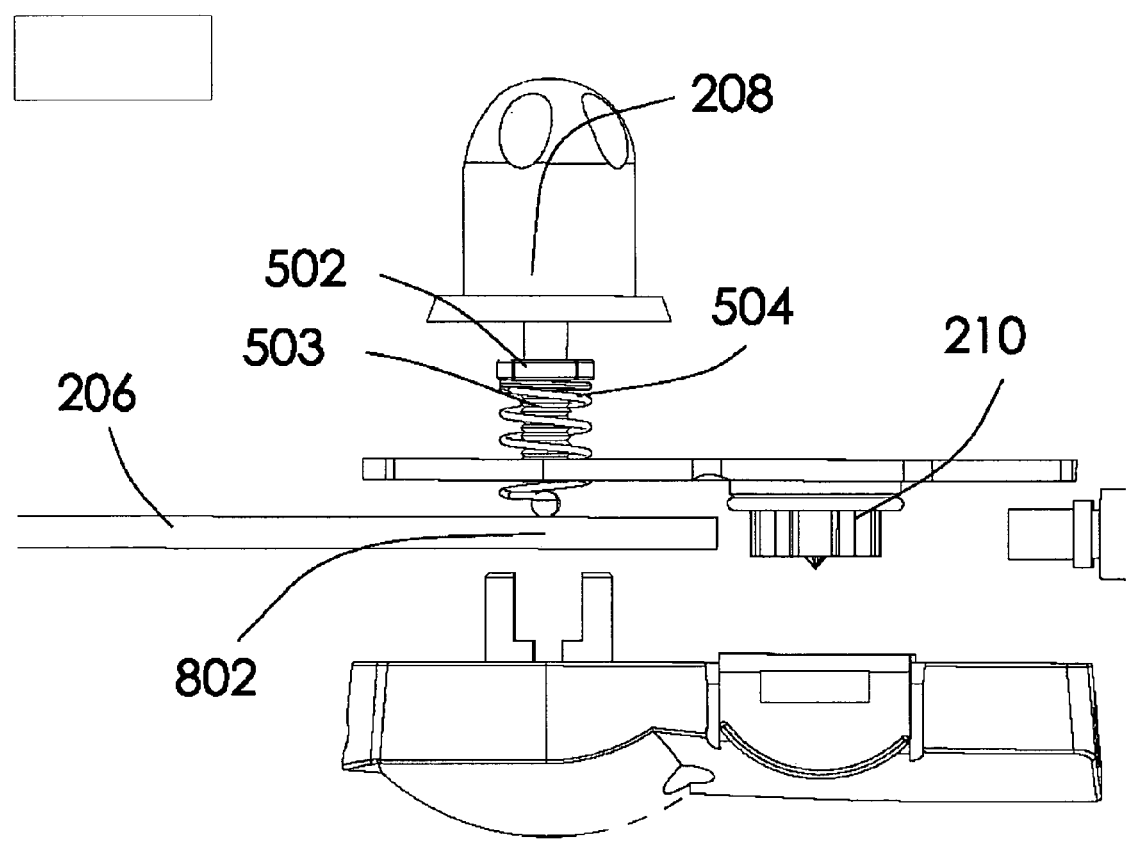

FIG. 8b provides a transparent view when the resistive component (pinch bar 414) is at its minimum. Resistance control knob 208 has been rotated to a position where advancing nut 502 is fully retracted along the length of threaded shaft 503, away from outlet tube 206. The force exerted by occlusion spring 504 is minimal and outlet tube 206 is fully open as shown at open lumen section of outlet channel 802.

Figure 8C:
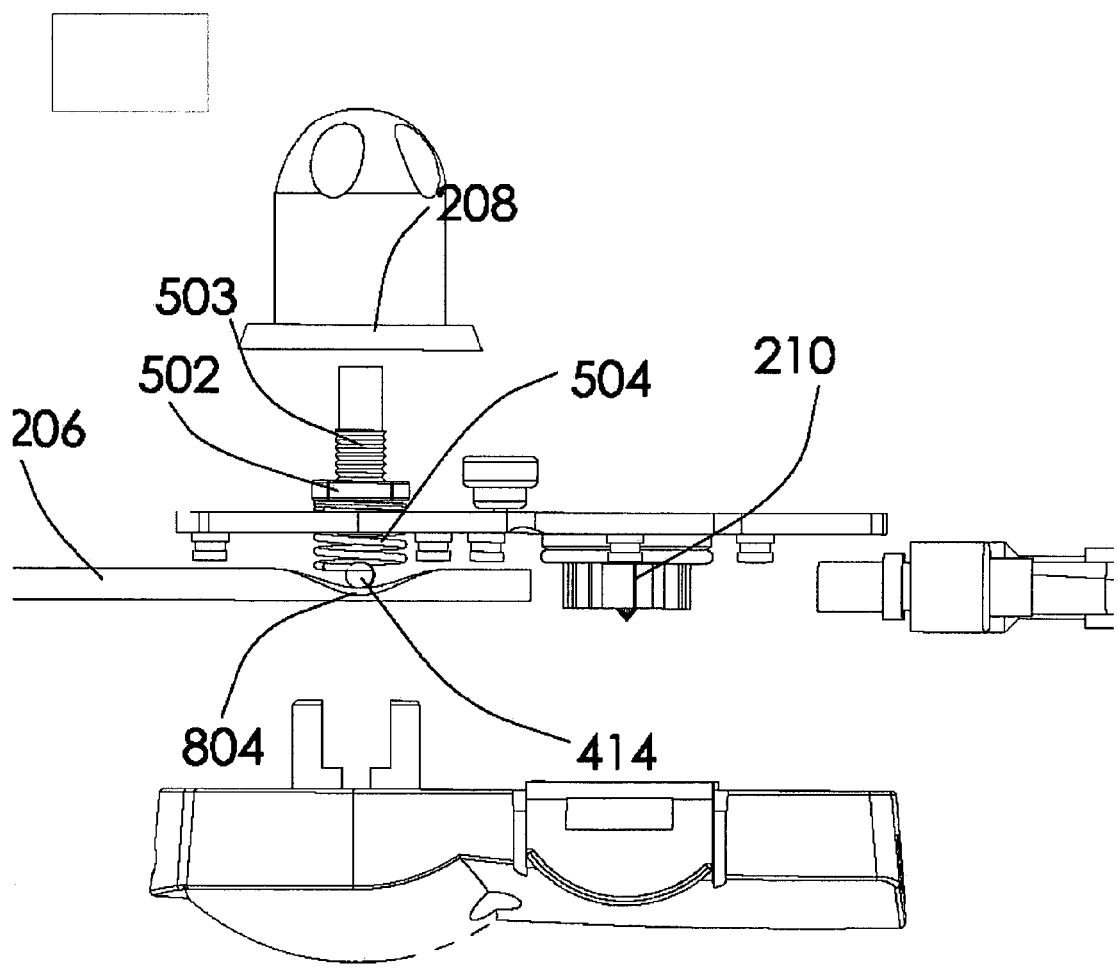

When the force of pinch bar 414 is at its maximum, outlet tube 206 is completely closed as shown at closed lumen section of outlet channel 804 in FIG. 8c. Advancing nut 502 is in its position along threaded shaft 503 that is closest to outlet tube 206, exerting a maximum compression of occlusion spring 504. In the embodiment shown in FIG. 8c, resistance control knob 208 has been adjusted to provide sufficient force to overcome the combined fluid pressure within the tube and resilient force of outlet tube 206.

Figure 9:
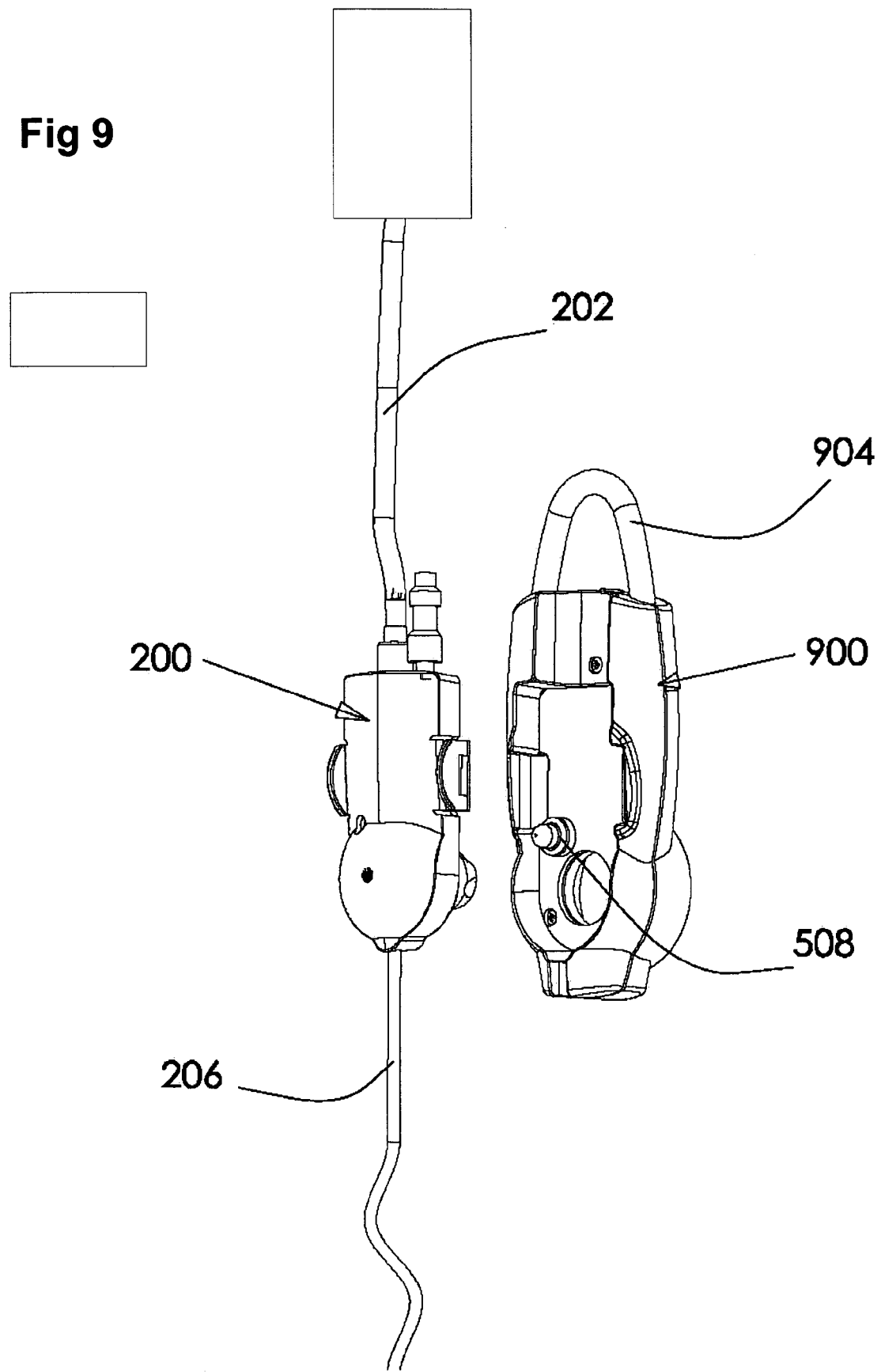
FIG. 9 is a transparent rear view of the cassette, juxtaposed with an opaque rear view of an automated flow control device ready to receive the cassette.

In FIG. 9, fluid pathway assembly 200 (shown originally in FIG. 1a) can snap into flow control device 900. Drive wheel 508 is driven by an internal motor (not shown) to use frictional interference to turn resistance control knob 208 on fluid pathway assembly 200. U-shaped hanger 904 across the top of the device is a flexible member used to suspend the device from a hook or clamp, such as on an IV stand.

Figure 10:
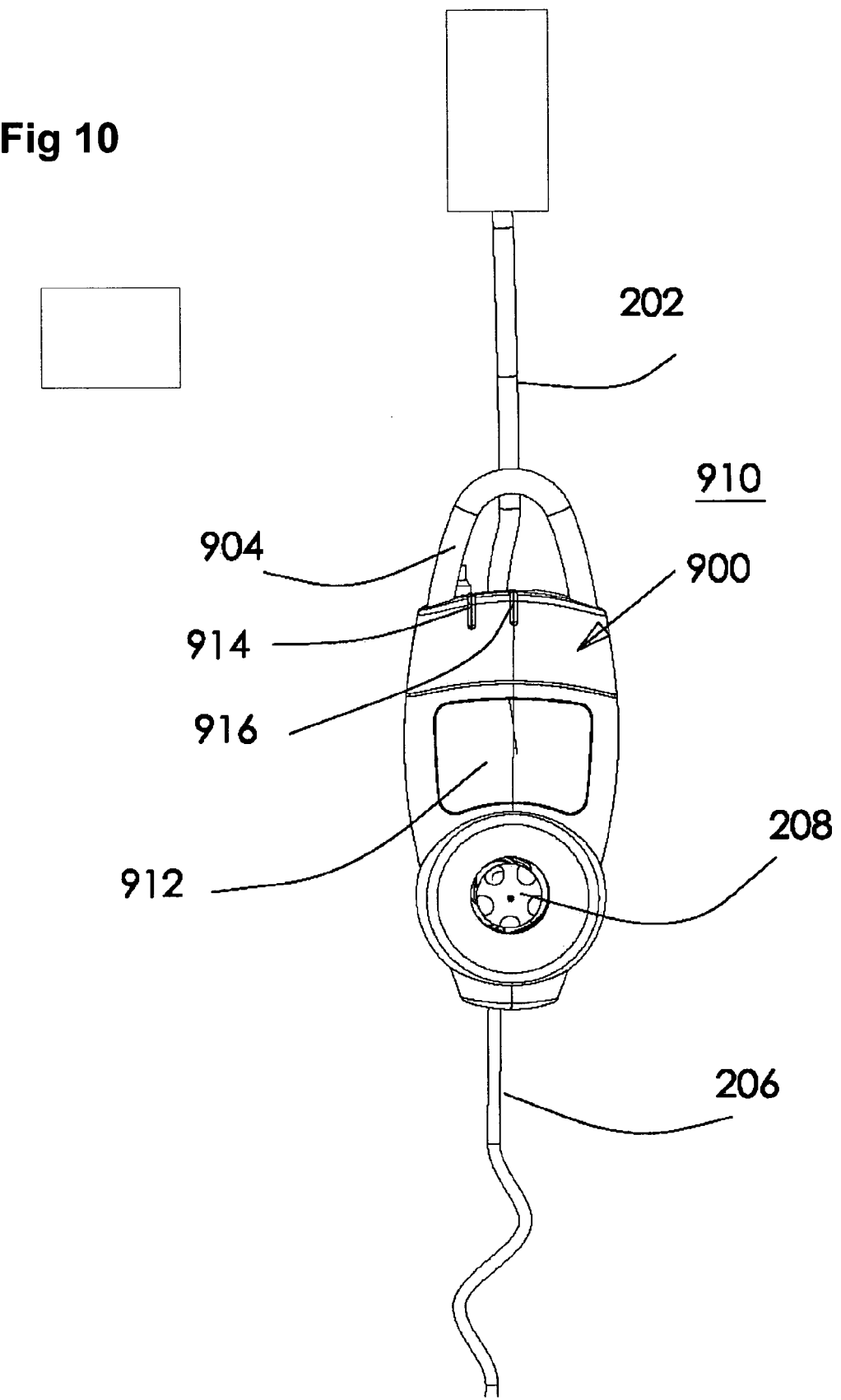
FIG. 10 is a front view of the cassette and flow control device of FIG. 9 snapped together, showing display features.
Figure 11:
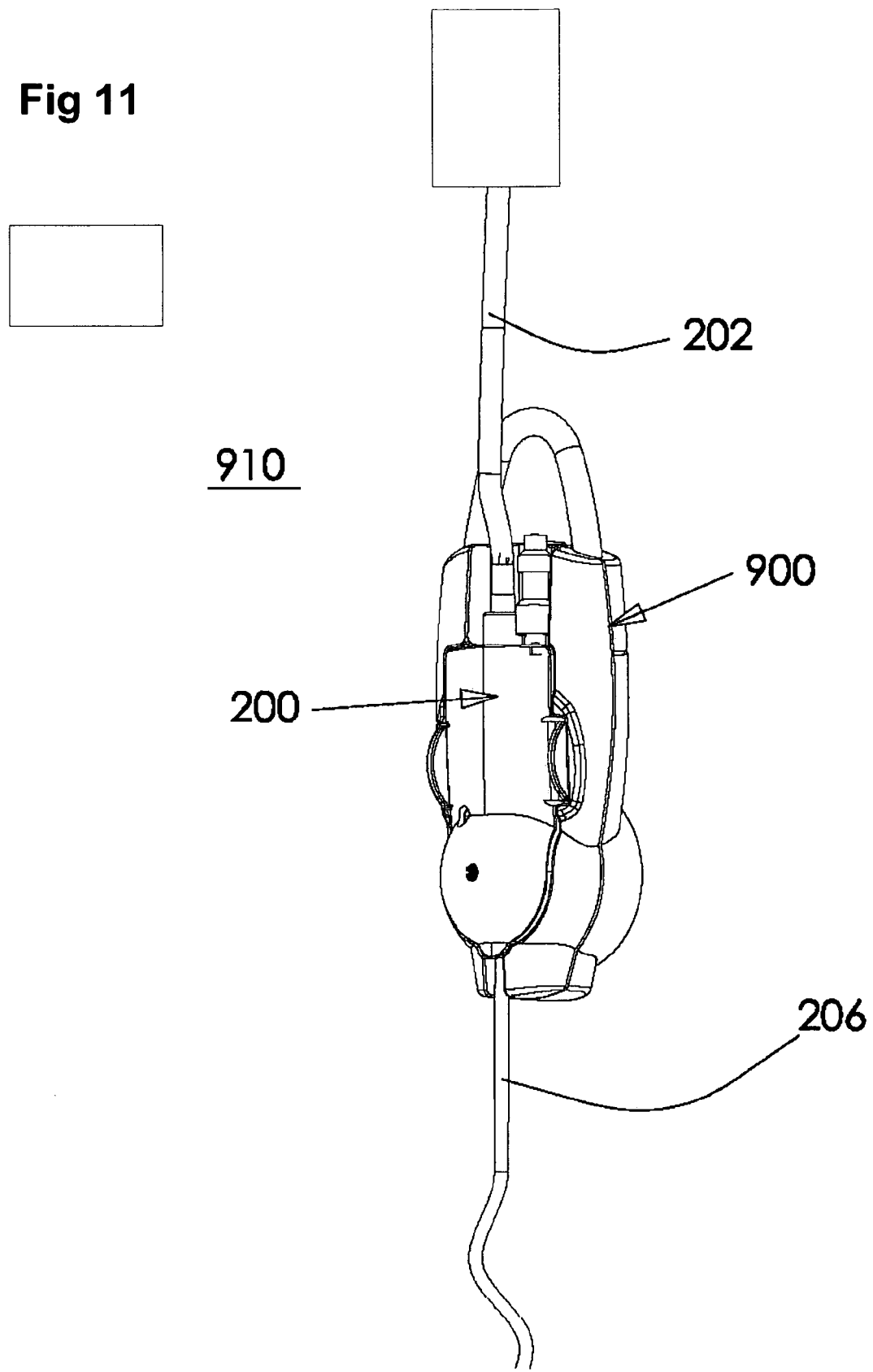
FIG. 11 shows a transparent rear assembly view similar to FIG. 10.

FIG. 10 illustrates fluid administration assembly or apparatus 910 which comprises fluid pathway assembly 200 and flow control device 900. The rear of fluid administration assembly 910 is shown in FIG. 11, enhanced by the transparency of fluid pathway assembly 200. In FIG. 10, the front of flow control device 900 is shown, in which most of the components of fluid pathway assembly 200 are hidden, except for resistance control knob 208, which protrudes through an opening in flow control device 900. Visual indications of flow and alarms for each fluid source are provided by secondary status light 914 and primary status light 916. Graphic display 912 provides other textual and graphic information to the user, depending on the application and context.

When fluid pathway assembly 200 is mated with flow control device 900 to form fluid administration assembly 910, resistance control knob 208 is still visible and available to the user. Fluid pathway assembly 200 may be removably mated with flow control device 900 via mechanical means known to those of ordinary skill in the art, such as, but not limited to snaps, hook and loop type fasteners (e.g., VELCRO®) and similar attachment mechanisms. The operator (e.g., a physician, nurse or medical technician) may watch in-line rotary flow impeller 210 or drop forming chamber 302 for an approximate indication of flow rate, and subsequently watch a digital readout of flow rate on graphic display 912 inferred from the rotation of in-line rotary flow impeller 210. When the operator releases resistance control knob 208, automatic control is restored, and the motor and gear system monitors and adjusts the fluid resistance to maintain the flow rate, compensating for changing conditions such as declining fluid head height (as the bag empties), changing position of the patient's body, and physical changes in the pinched tube related to temperature and plastic creep.

If a secondary infusion is started via secondary fluid source connection receptacle 204, the operator may set a different flow rate for that infusion. The servomechanism will then maintain that flow rate in the secondary direction, until the impeller reverses direction, indicating depletion of the secondary source. The servomechanism can be programmed to respond to this flow direction reversal by using adjusting gear motor 506 to re-adjust resistance control knob 208 to restore the rate originally set for the primary infusion. Buttons or keys on the controller are not needed and control for the two flow rates is intuitive. The automatic transition from a secondary infusion to a primary infusion, upon depletion of the secondary fluid source has not heretobefore been disclosed in the art, and is made even more valuable by the simple and intuitive user interface.

In an alternative embodiment, control of resistance can be achieved entirely via adjusting gear motor 506 and drive wheel 508. When the operator turns resistance control knob 208, the effect is to control a visual indicator, such as graphic display 912, causing it to show the desired rate. The servomechanism then causes the actual rate to match the dialed-in rate. If for some reason the servomechanism is unable to achieve the dialed-in rate, the indicator can show the actual, incorrect rate (for example, zero rate with a blocked line or depleted source) while simultaneously broadcasting an alarm signal (for example, using secondary status light 914 or primary status light 916).

Note that flow control device 900 provides a uniquely simple interface, as shown in FIG. 10. There are no electronic controls, in stark contrast to a conventional flow control device with a myriad of buttons or software interactions. The only control available to the user in accordance with the present invention is a mechanical control in the form of resistance control knob 208, which is part of fluid pathway assembly 200. A turn of resistance control knob 208 will alter the fluid flow resistance, as illustrated schematically by variable resistance 134 in FIG. 1a. As discussed repeatedly, resistance control knob 208 may also be moved as a result of the rotation of drive wheel 508, caused by activation of adjusting gear motor 506. Based on the familiar symmetry of an electromagnetic sensor and driver, a motor, such as adjusting gear motor 506, may also be used as a sensor. In this case, integrated circuitry 944 may be used to observe the signals from adjusting gear motor 506 to determine whether resistance control knob 208 had been turned from an external source, such as a user. By detecting the induced voltages on adjusting gear motor 506, integrated circuitry 944 can infer that resistance control knob 208 has moved.

Figure 12A:
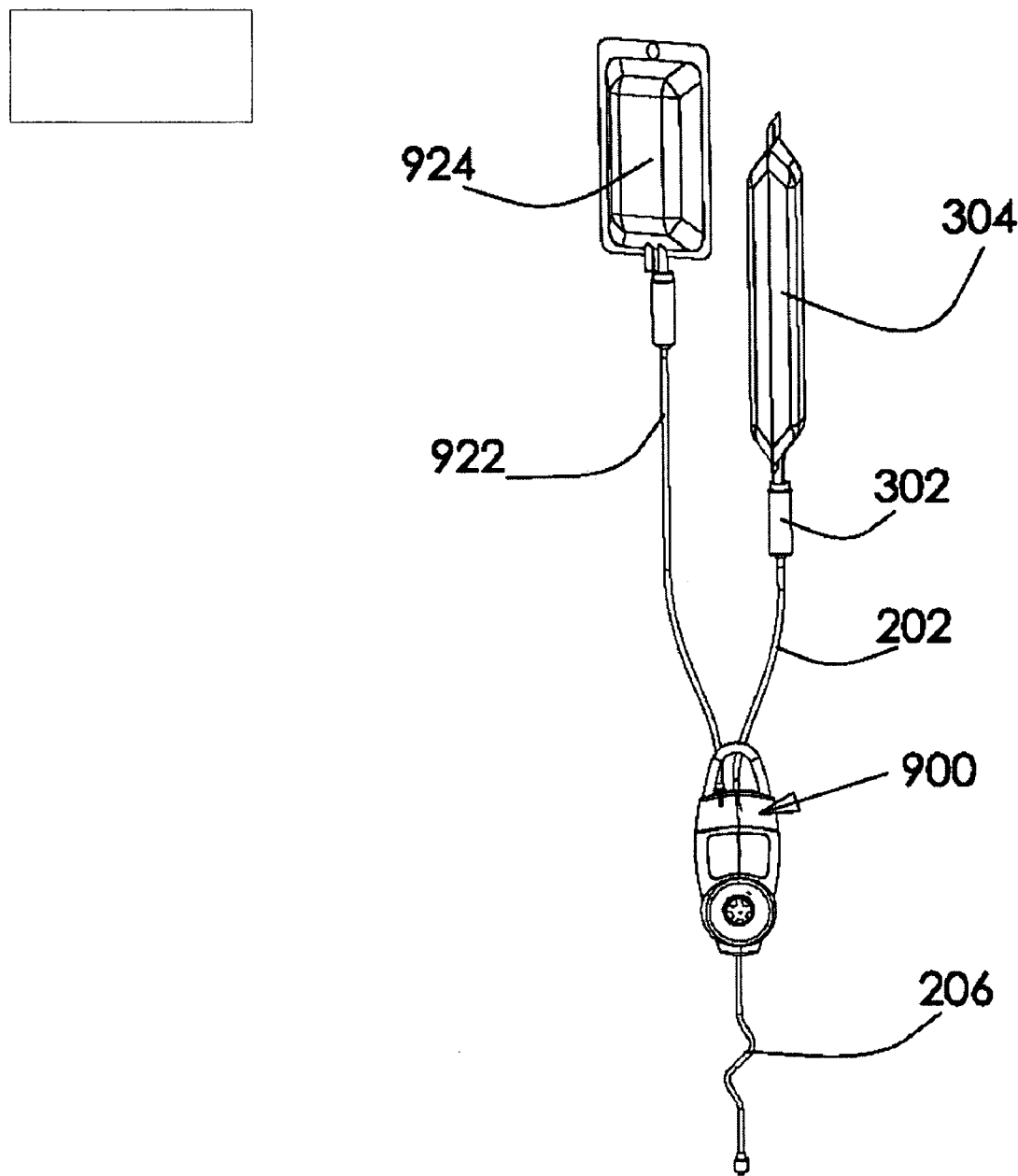
FIGS. 12a and 12b show a complete realization of the system of FIG. 1a, with views of primary and secondary source bags in 12a and a close-up transparent rear view in FIG. 12b.
Figure 12B:
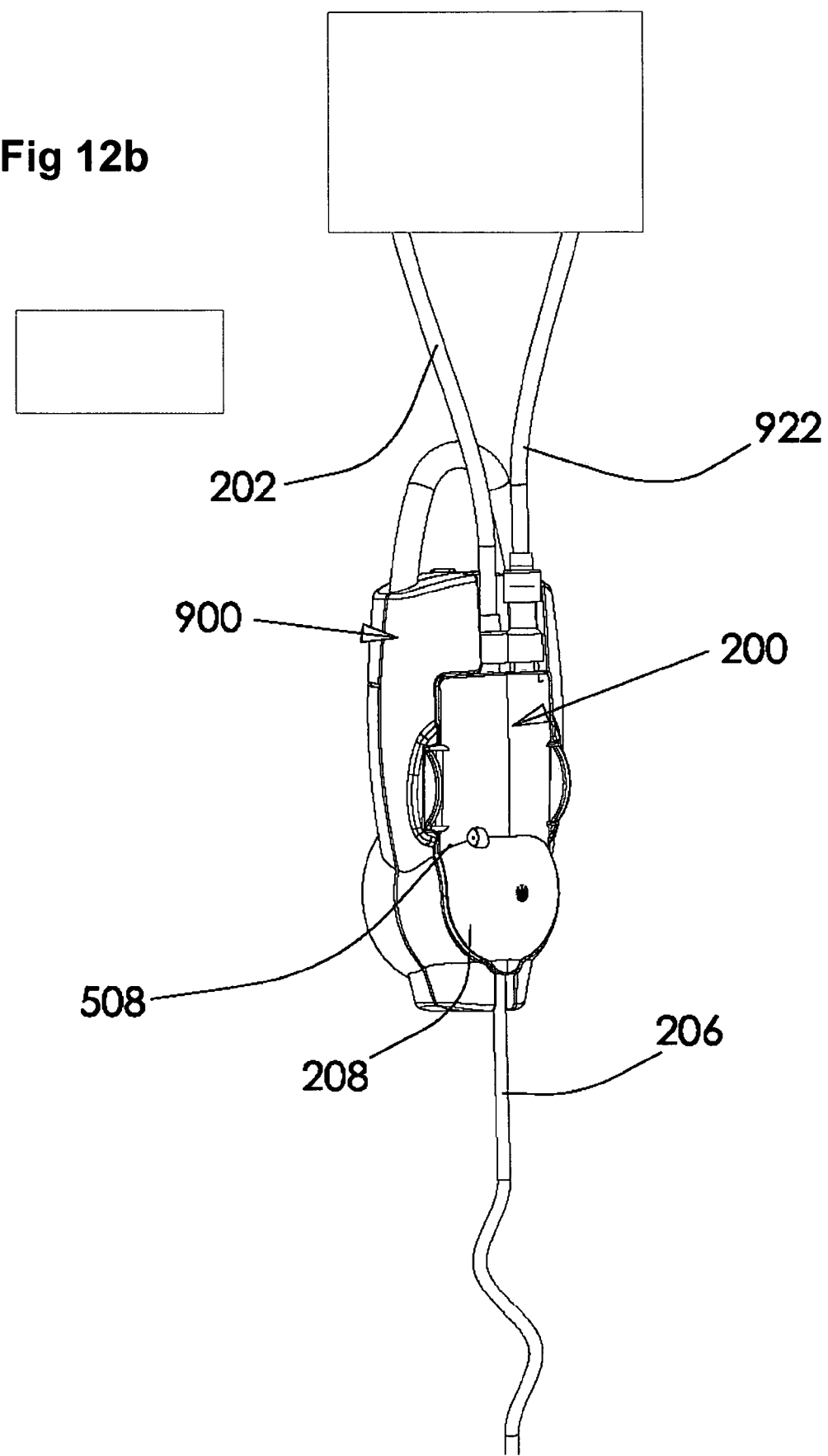

A front plan view shown in FIG. 12a incorporates the major elements of fluid administration system 100 shown schematically in FIG. 1a. In addition to previously shown elements, drop forming chamber 302, and primary fluid reservoir 304, FIG. 12a shows secondary fluid reservoir 924 and secondary inlet line 922. The position of secondary fluid reservoir 924 is shown higher than primary fluid reservoir 304, so that the internal pressure of secondary fluid reservoir 924 will cause primary one-way valve 402 (FIG. 4) to close. A reverse view of FIG. 12a is shown in FIG. 12b, illustrating the relative positions of secondary inlet line 922 and secondary fluid reservoir 924.

Figure 13:
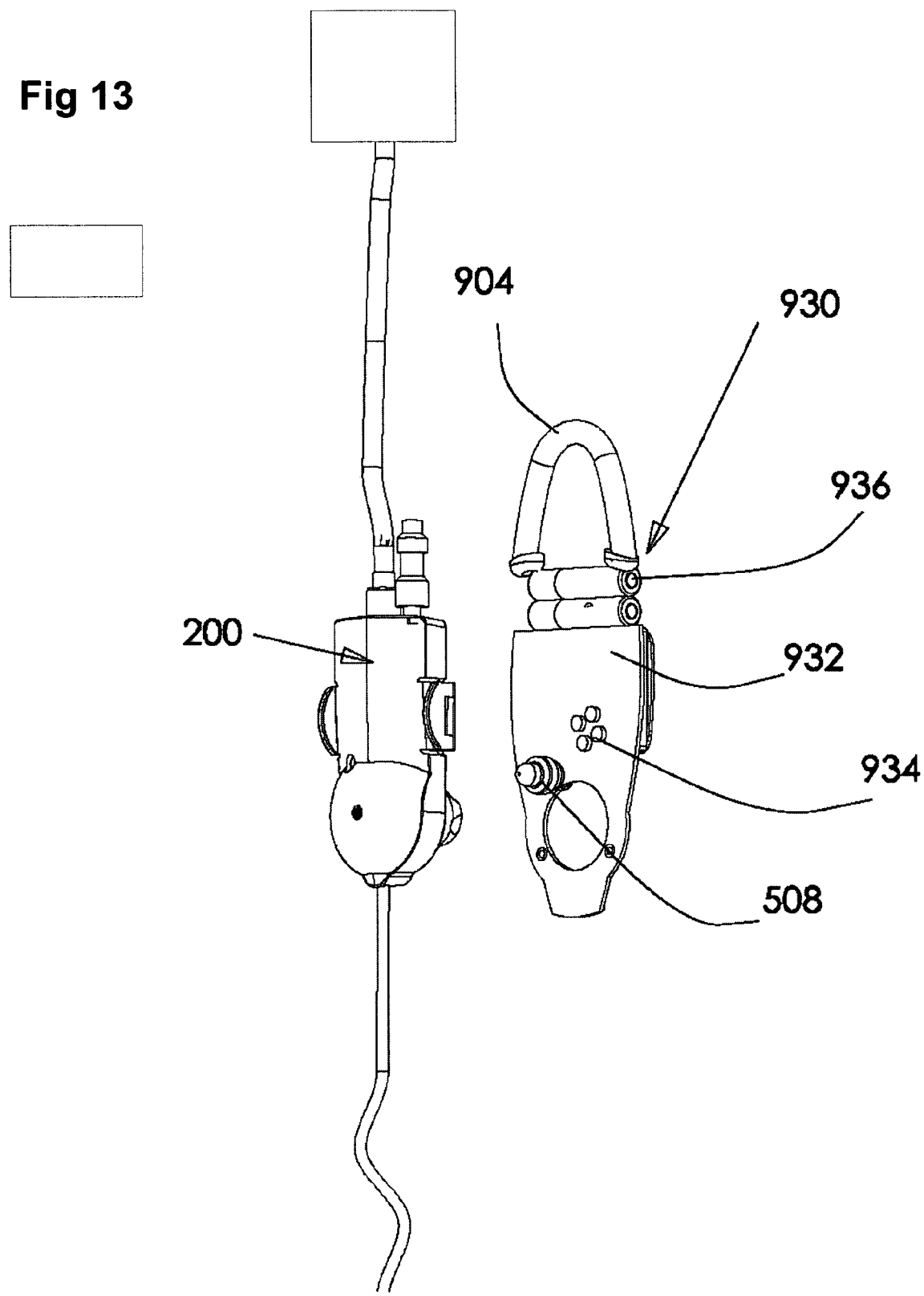
FIG. 13 is an exploded view similar to 11 with the chassis of the device removed to reveal the functioning subassembly.

The interior of flow control device 900 is revealed in the perspective view of FIG. 13 by removing the exterior shell (not shown) and showing flow control device subassembly 930. Within flow control device 900, set of electromagnetic coils 934 are attached to printed circuit board 932 and which are powered by batteries 936. Drive wheel 508 is visible from this view as well.

Figure 14:
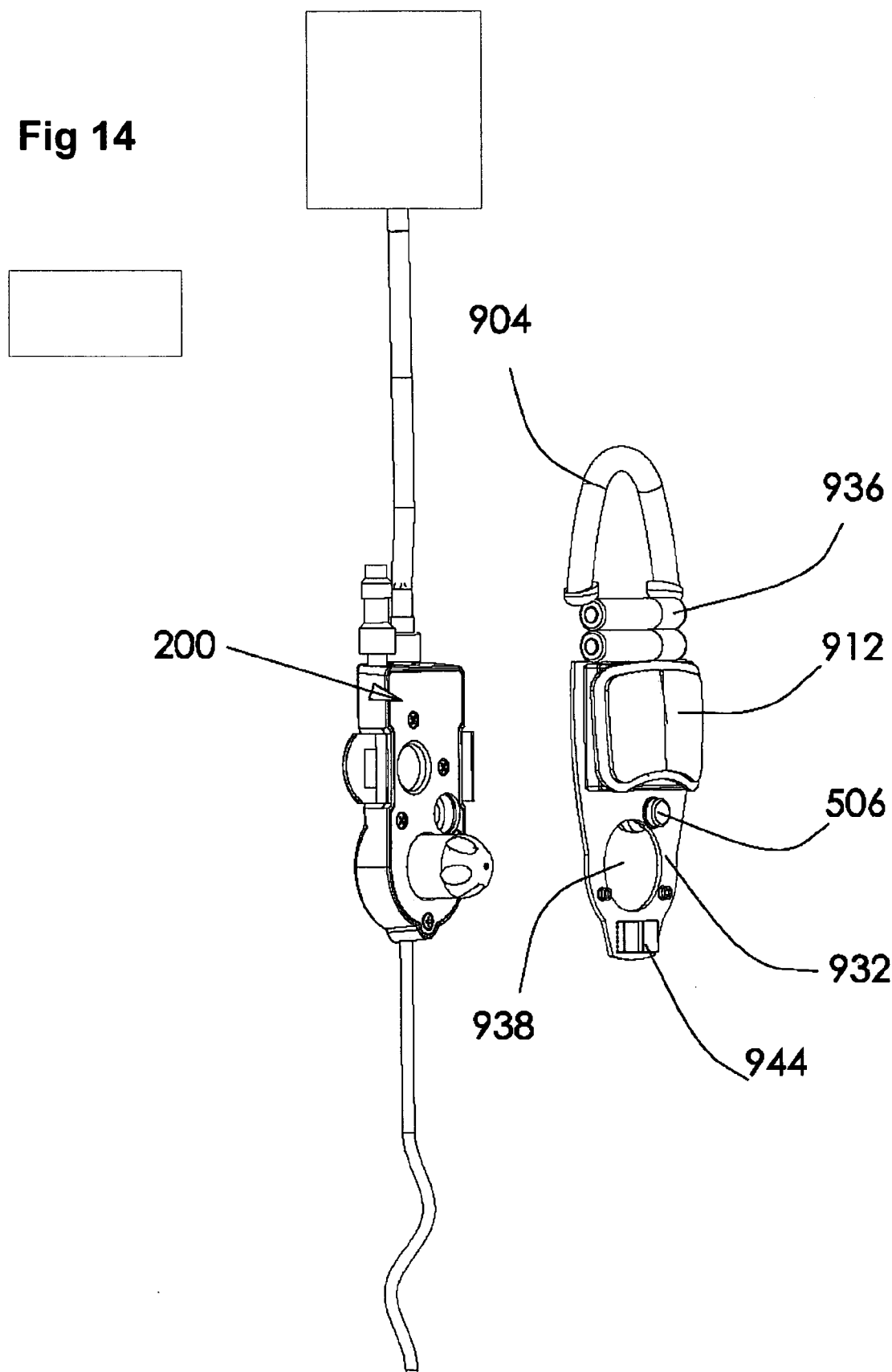
FIG. 14 is similar to FIG. 13 from the reverse side.

FIG. 14 illustrates the reverse perspective view of FIG. 13 in which graphic display 912, first shown in FIG. 10, is visible as connected to printed circuit board 932. Adjusting gear motor 506 is also a component of printed circuit board 932, as is integrated circuitry 944. The central hole 938 of printed circuit board 932 accommodates the position of resistance control knob 208 when fluid pathway assembly 200 and control device 900 are mated together.

Figure 15:
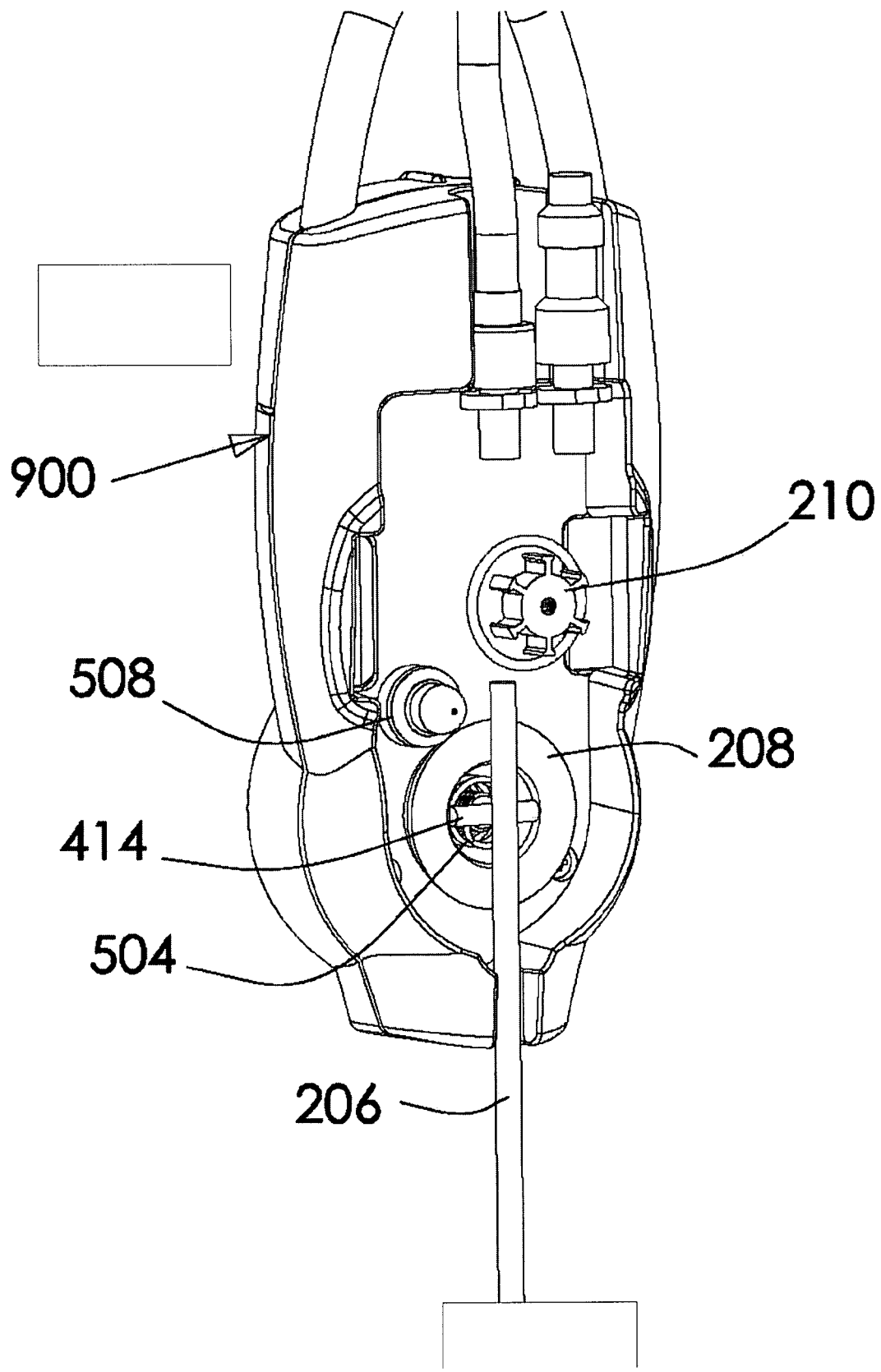
FIG. 15 is a perspective view of the two major assemblies shown together.
Figure 16:
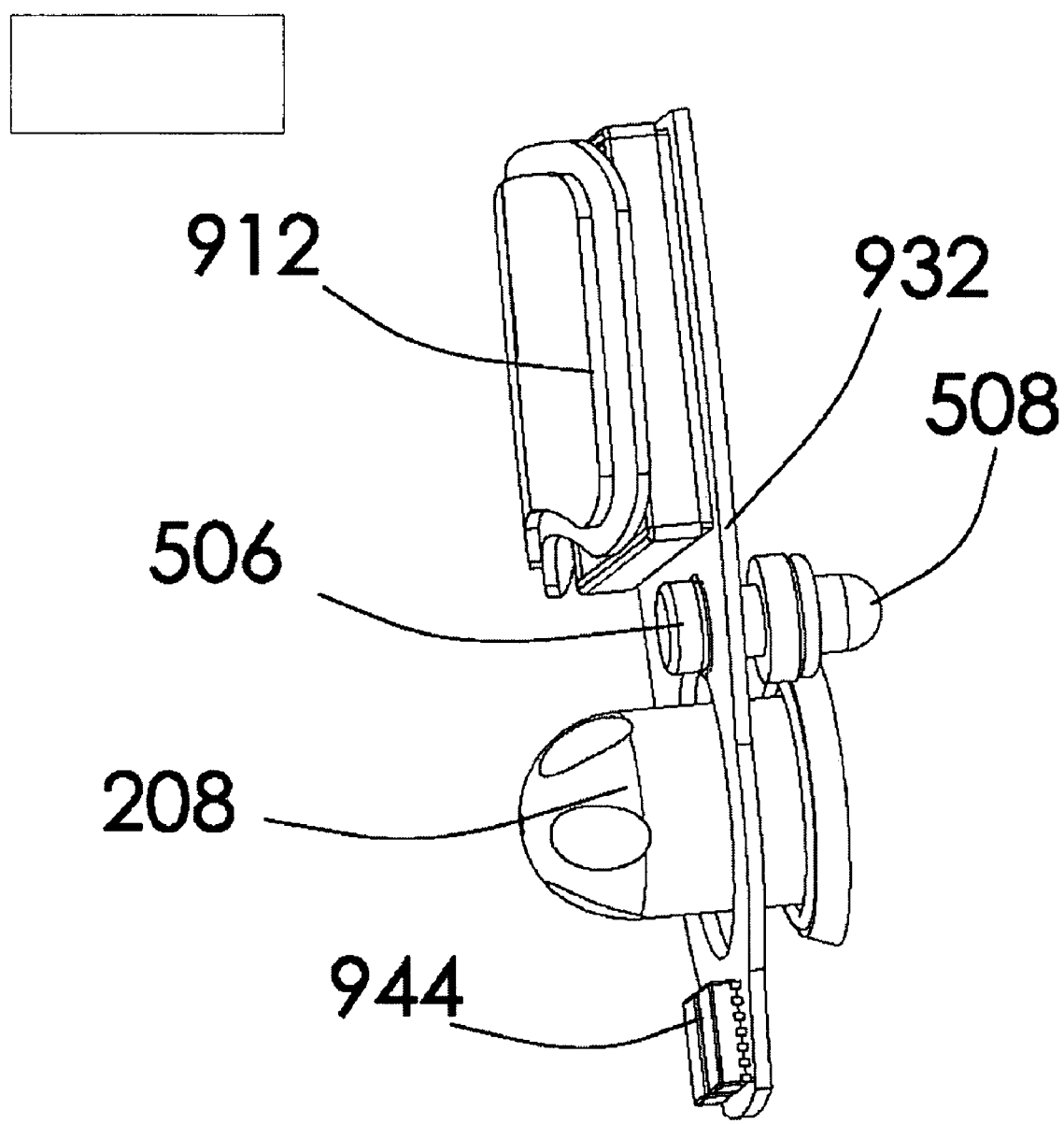
FIG. 16 is a perspective view of the device subassembly.

FIG. 15 illustrates a close up perspective view of the elements of fluid pathway assembly 200 when mated with flow control device 900. The rear side of resistance control knob 208 is visible as is occlusion spring 504 as it presses upon pinch bar 414. The force of pinch bar 414 occludes a section of outlet tube 206, creating a fluid flow resistance. Outlet tube 206 is pressed by pinch bar 414 on one side and pressed against the fixed chassis part of fluid pathway assembly 200, which is hidden to allow the view of the interior. In-line rotary flow impeller 210 is shown for reference. The frictional relationship between drive wheel 508 and resistance control knob 208 is seen in this view. This frictional relationship is more easily seen in FIG. 16, along with integrated circuitry 944, adjusting gear motor 506, printed circuit board 932, and graphic display 912 (shown for reference).

Figure 17:
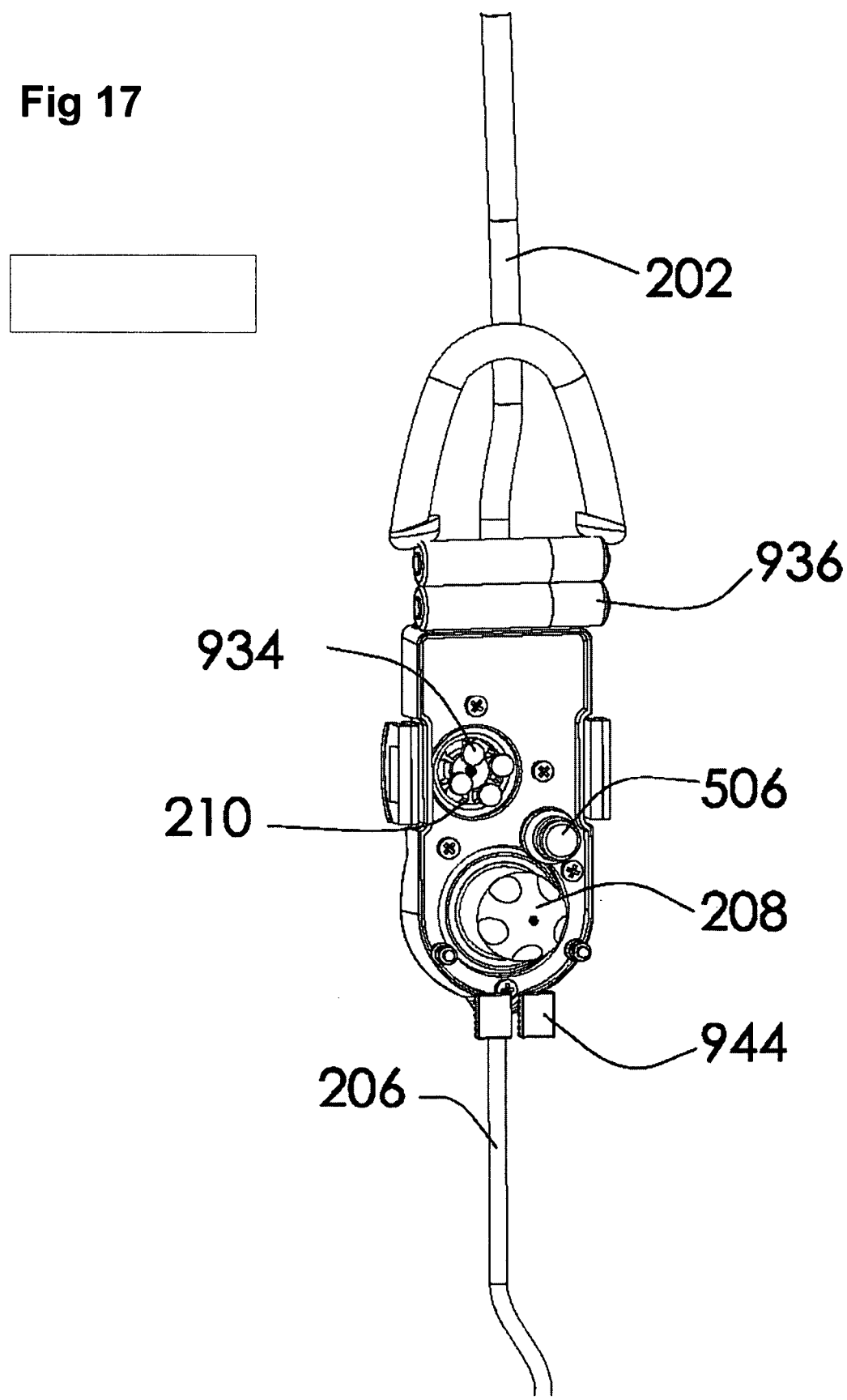
FIG. 17 is a plan view of the two major assemblies shown together with the cassette shown as transparent.
Figure 18:
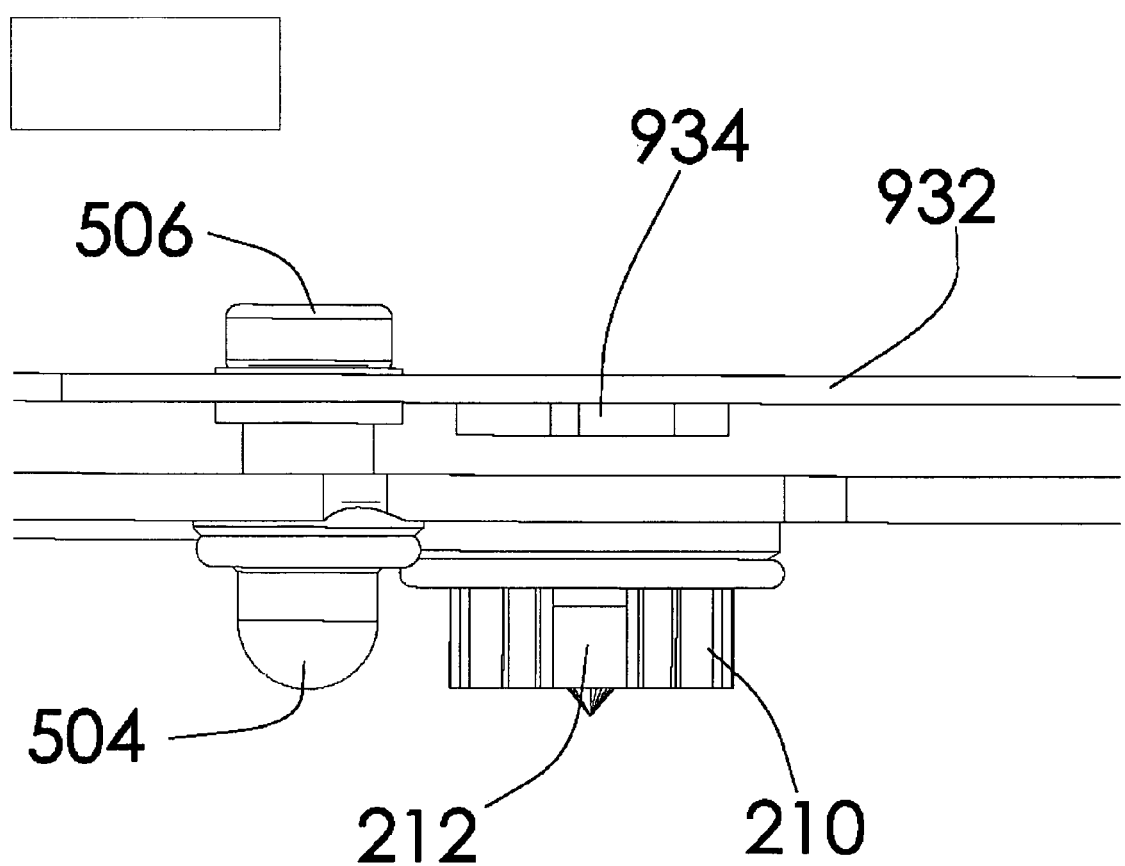
FIG. 18 is a close up cross sectional view of the two major electromagnetic subassemblies shown together.

A transparent front plan view of fluid administration assembly 910 is shown as FIG. 17, which illustrates the relationship between set of electromagnetic coils 934 and in-line rotary flow impeller 210. This relationship is amplified in FIG. 18, where set of electromagnetic coils 934 is shown parallel to the face of in-line rotary flow impeller 210. The cross section of in-line rotary flow impeller 210 reveals the embedded permanent magnet 212 (previously shown in an exploded view in FIG. 6). The configuration of set of electromagnetic coils 934 can be such that the application of power to various combinations of coils can generate a vector that attracts or repels permanent magnet 212, causing movement of in-line rotary flow impeller 210. Set of electromagnetic coils 934 may be used as a sensor of changing magnetic fields or as the producer of a known magnetic field, or in a fashion where driving and sensing duties are multiplexed.

Figure 19:
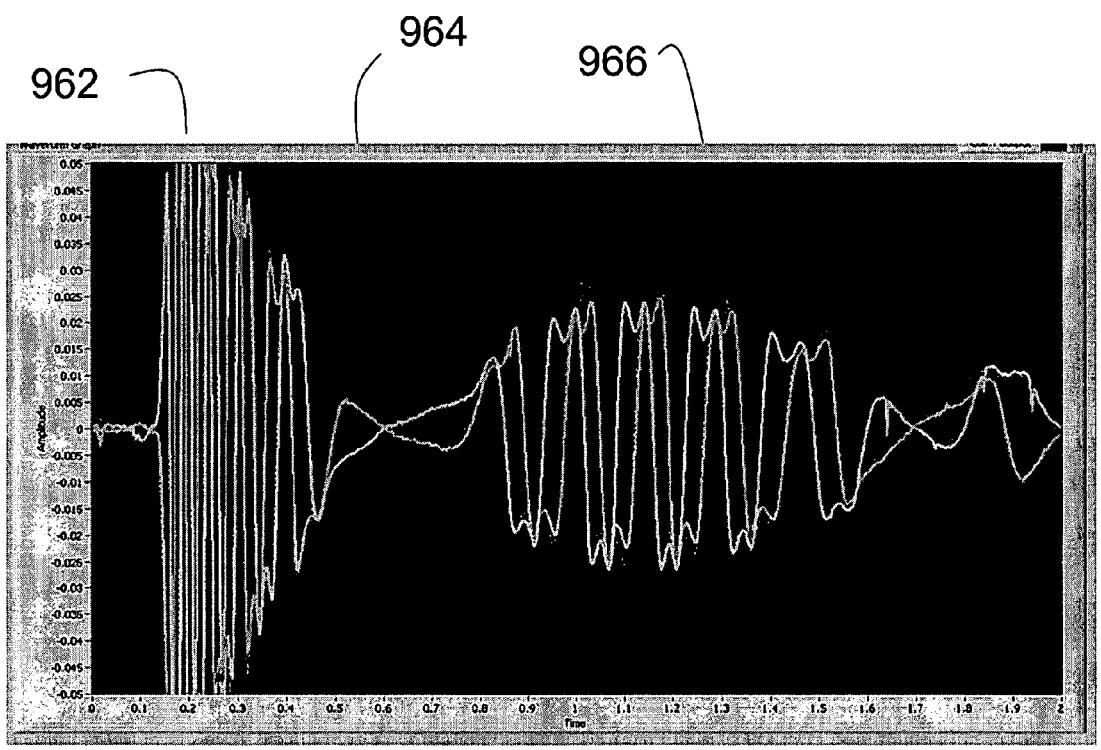
FIG. 19 is a chart of the passive electromagnetic response of the magnetic impeller.

Measurements of such a system are illustrated in FIG. 19 in which voltages taken from set of electromagnetic coils 934 are appropriately amplified and displayed, as fluid is moved through fluid pathway assembly 200. Coil response to rapid clockwise movement of magnet 212 is a measurement taken when fluid enters primary inlet line 202 and causes the rotation of in-line rotary flow impeller 210. The rotation of in-line rotary flow impeller 210 causes a spinning movement of permanent magnet 212 whose moving magnetic field induces a current in set of electromagnetic coils 934. At point transition of rotation of magnet 212, an injection of fluid was made with bolus administration syringe 702, creating a higher pressure in bolus administration syringe 702 than in primary inlet line 202 and closing flow across primary one-way valve 402. The flow is then directed through connection receptacle for secondary fluid source 204 to outlet tube 206, via secondary channel 406, in-line rotary flow impeller 210, and outlet channel 412. The direction of this flow effectively reverses the direction of in-line rotary flow impeller 210, first stopping as shown in area transition of rotation of magnet 994 and then going in the reverse direction as shown in coil response to slower counterclockwise movement of magnet 212. FIG. 19 represents the passive observation of relatively high fluid flow rates.

Figure 20:
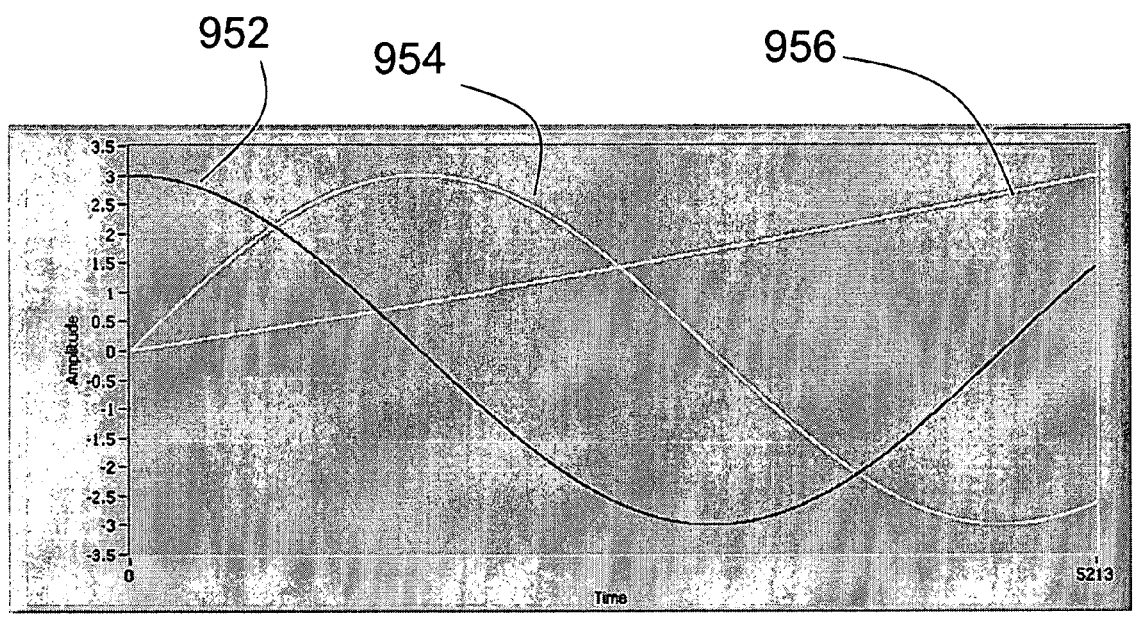
FIG. 20 is a chart of the driven electromagnetic response of the magnetic impeller.

Slower flow rates employ a combination of driving and sensing the fluid flow. In FIG. 20, set of electromagnetic coils 934 is energized by a protocol determined within integrated circuitry 944 and powered by batteries 936. In this configuration, one pair of coils is oriented in series in a north-south conformation and another pair is in series in an east-west conformation. The voltages applied to each pair are shown as signal drive on N-S coil pair 952 and signal drive on E-W coil pair 954. The timescale of these voltage transitions may be very long, relative to the potential speed of the electronics. In this example, a period of three minutes is shown as elapsed time in minutes 956.

Figure 21:
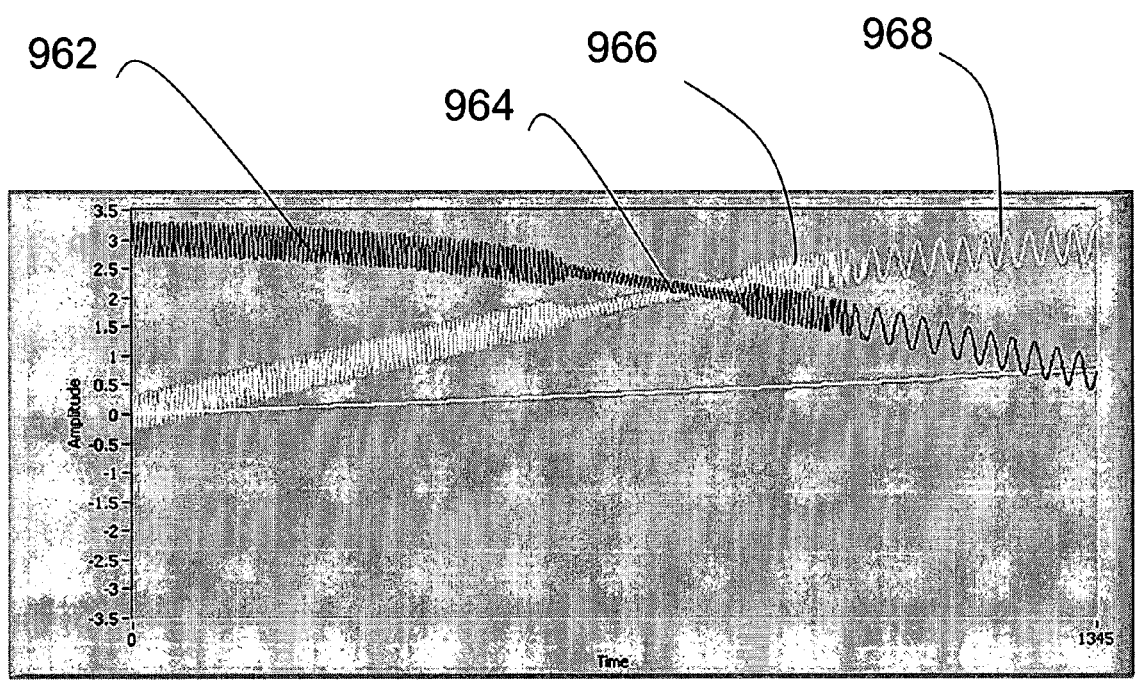
FIG. 21 is a chart of the modulated electromagnetic response of the magnetic impeller.

A steady state electromagnetic field may be imposed using set of electromagnetic coils 934, as shown in FIG. 20. FIG. 21, however, illustrates the potential to apply alternating current modulation to these slowly modulating vectors. Rapid modulation of N-S coil pair 962 indicates a relatively strong and relative fast modulation of a slowly changing magnetic field. That same speed of modulation is shown with reduced amplitude as reduced modulation of N-S coil pair 964. Rapid modulation of E-W coil pair 966 shows that the modulation can be made on either pair of set of electromagnetic coils 934. The speed of the modulation can be increased or decreased, as shown as slower modulation of E-W coil pair 968. The ability to drive permanent magnet 212 with set of electromagnetic coils 934 and to reciprocally sense the motion of permanent magnet 212 with set of electromagnetic coils 934, provides a broad range of interactions that can be used to determine underlying flow rates, impedances, compliances, and resistances.

Figure 22:
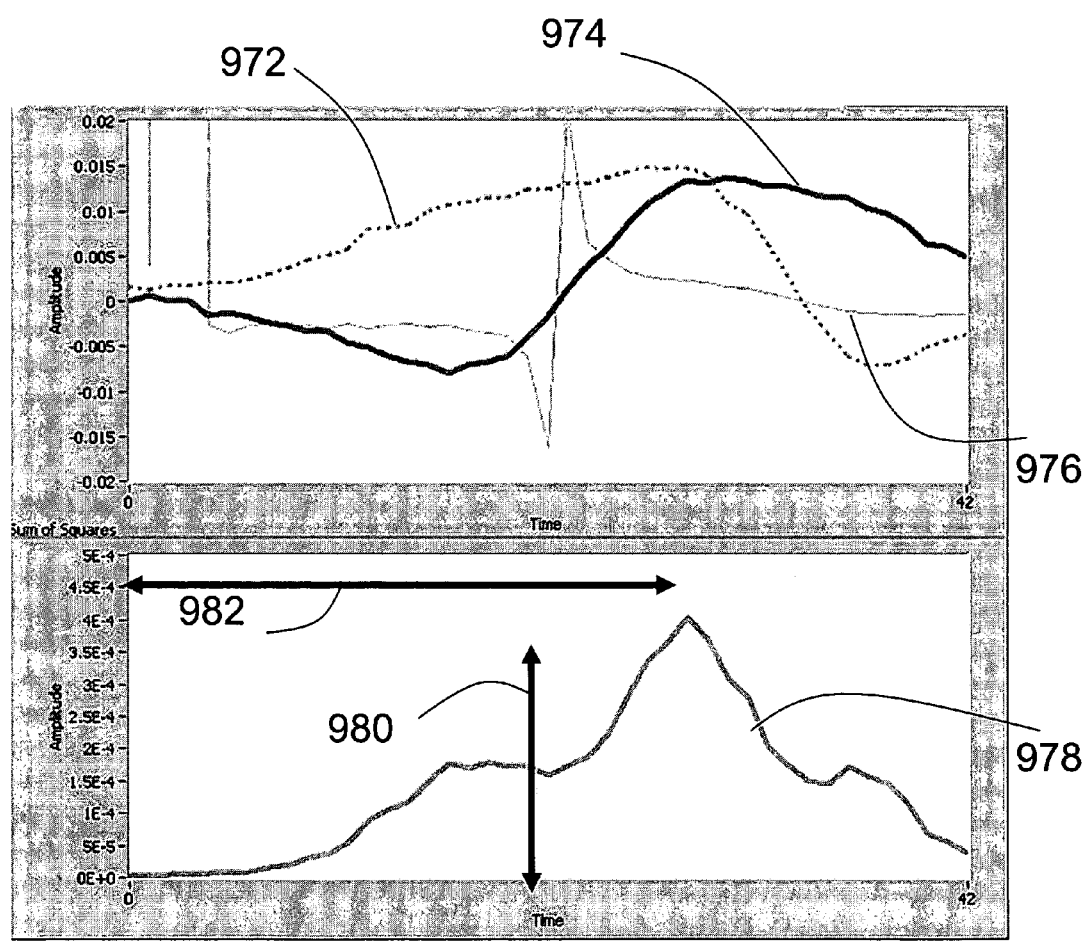
FIG. 22 is a chart of the electromagnetic response of the magnetic impeller.

The results from a brief electromagnetic pulse, followed by a period of "reading" or sensing the movement of permanent magnet 212 are shown FIG. 22. The E-W coil response 972 to rapid pulse of magnet shows the resultant voltage induced one leg of set of electromagnetic coils 934. The other leg is shown as N-S coil response 974 to rapid pulse of magnet. The ratio of the two measurements results in a vector that indicates the position of permanent magnet 212. With a constant speed of angular rotation, for example, when the signal is maximal with respect to the N-S orientation of coils, then it means that the signal will be zero with respect to the E-W coils. The relative voltages of coil pairs indicate angular position, as shown by ratio of coil pair responses 976.

The angular velocity is equal to the sum of the squares of orthogonal coil pairs. This computation is shown as angular velocity 978. Following a known magnetic impulse, it would be useful to compute the speed created by the imposed vector. Maximum angular velocity 980 provides the indication of maximum angular velocity. There are several measurements of interest in the time domain as well. One measurement, shown by way of example, time of maximum velocity 982, indicates how long it took for permanent magnet 212 to reach it maximum velocity. Measurements made as shown in FIG. 22 are typically made in fractions of seconds.

A major feature of the present invention is the quasi-static nature of the control loop. Once resistance control knob 208 has been established at a position that achieves the targeted flow rate, resistance control knob 208 is maintained in one spot to maintain said rate. Adjustments to resistance control knob 208, though the activation of adjusting gear motor 506, are required only in response to external changes in fluid pressure and resistance. The infrequent use of a motor is a key ingredient to conservation of power, which has high importance for a battery operated device. The periodic observation of in-line rotary flow impeller 210 by integrated circuitry 944 requires negligible energy consumption.

In accordance with the present invention, the apparatus of the invention affords the utilization of a sensor and an actuator with greater range and far higher degrees of resolution than was previously available. Additionally, the present invention provides for the use of quasi-static settings to provide the opportunity for vast reductions in energy consumption. The feature of high resolution for control comes from three characteristics of adjusting gear motor 506. First, adjusting gear motor 506 must be capable of moving in very small steps, certainly resulting in less than one micron of tube compression per step. Second, when the movement of said adjusting gear motor 506 has stopped, said motor must stay at the spot where movement stopped so there is no measurable backlash or mechanical hysteresis. Finally, adjusting gear motor 506 should have the ability to maintain its position without the expenditure of any additional energy.

Power consumption and required battery weight in this system can be made very low, due to the mode of operation. The flow rate need only be monitored intermittently, so that parts like integrated circuitry 944 and set of electromagnetic coils 934 need not be run continuously. Flow is propelled by gravity or by a pressurized container, rather than by pumping. Once set, fluid resistance is relatively stable, so adjusting gear motor 506 is activated only with a very low duty cycle to make small adjustments. Thus, in typical operation, integrated circuits 944 are responsive to an operator turning resistance control knob 208. Integrated circuits 944 are active until the operator has set a rate and that rate has been stabilized by the servo. The entire system then shuts down excepting for a wakeup timer that re-activates the microprocessor and pulses power to the flow measurement device, as needed to check the flow rate. On a given timed check, the control motor may require activation long enough for a small rate adjustment or may not be needed.

In one embodiment, the contained volume of in-line rotary flow impeller 210 is about 50 microliters. The rotational sensitivity of set of electromagnetic coils 934 is greater than 250 parts per revolution, yielding a sensitivity of movement on the order of 0.2 microliters (50 microliters per revolution divided by 250 counts per revolution). This sensor resolution compares favorably to the highest resolution "drop size" of $\frac{1}{60}$th of a ml or 17 microliters.

Furthermore, a "drop counting" method does not support rapid flow rates and the user's ability to count rapid drops is limited as drops begin to merge or "stream" at higher flow rates. The present invention supports flow rates that are higher than those using drop counting methods. The ability of in-line rotary flow impeller 210 and integrated circuitry 944 to process information quickly is appreciated and known to be many orders of magnitude greater than the human. A nominally very high flow rate of 3,600 ml/h can be expressed as 1,000 microliters per second or nominally 20 revolutions per second of in-line rotary flow impeller 210. At 20 revolutions per second, integrated circuitry 944 would be required to service all of its functions in a period of 50 milliseconds. Commonly used microprocessors have many orders of magnitude of excess processing capacity for said task.

In an alternative embodiment, the sensing design provides a substitute for electromagnetic interactions. If in-line rotary flow impeller 210 were optical in nature, instead of magnetic, the rotary response of in-line rotary flow impeller 210 could be observed. The nature of the rotary encoder is not critical to this invention, so long at it reflects the true rotation of in-line rotary flow impeller 210.

Figure 23:
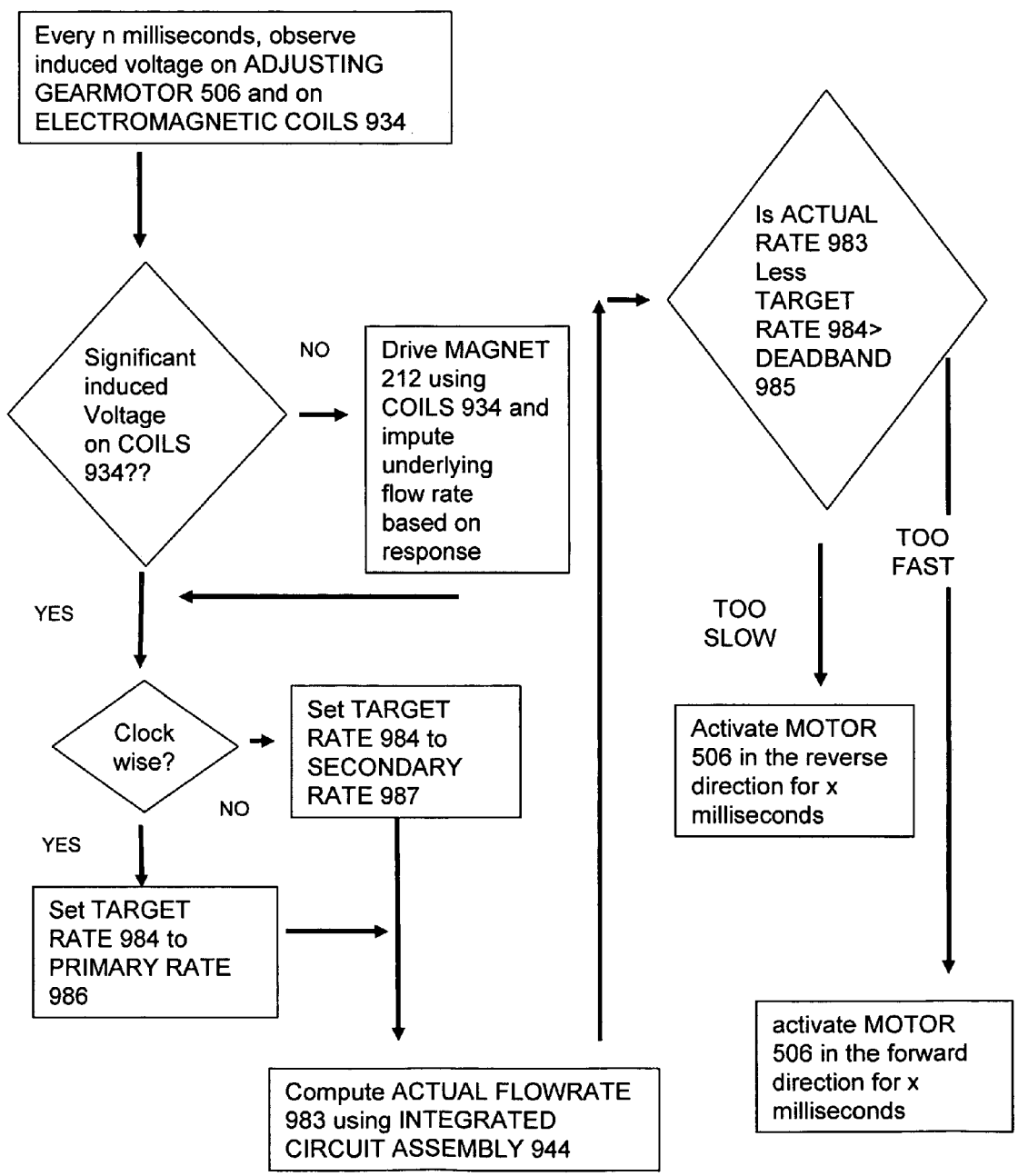
FIG. 23 is a flow chart of the operations that comprise the rate control method.

FIG. 23 shows a basic control strategy to maintain flow rate at a targeted level, even in the presence of changing pressures and resistances. Integrated circuitry 944 is periodically activated to observe the voltages seen on set of electromagnetic coils 934. If these voltages are significant, then there is movement of permanent magnet 212 within in-line rotary flow impeller 210. The pattern of induced voltages, as seen in FIG. 19, can be used to compute the rotational speed of in-line rotary flow impeller 210. This speed can be empirically correlated with underlying fluid flow rates and stored as a value in integrated circuitry 944 as actual rate 983. As shown in FIG. 19, the pattern of voltages indicates the direction of rotation for in-line rotary flow impeller 210. If the rotation is in the clockwise direction, then the fluid source is presumed to be from primary inlet line 202 and target rate 984 is set to a stored value primary rate 986. If the rotation is in the counterclockwise position, then the fluid source is presumed to be from connection receptacle for secondary fluid source 204 and target rate 984 is set to a stored value secondary rate 987. A certain degree of error is allowed in the flow rate control. If the flow rate error, represented by the difference between actual rate 983 and target rate 984, is greater than the allowed error, deadband 985, then positive feedback will occur in the form of activating adjusting gear motor 506, as explained in FIGS. 8a, 8b, and 8c. The quasi-static nature of the feedback control can be noted here. The position of resistance control knob 208 is adjusted as needed and periodically. If the physical conditions of fluid flow are stable, then the targeted flow rate will be maintained without any activation of adjusting gear motor 506. Consequently, if fluid pathway assembly 200 is removed from flow control device 900, the flow rate will not be altered, but will be subject to drift if flow conditions change. This feature of maintaining flow rate when the administration set is removed from the device is novel and very useful clinically.

Figure 24A:
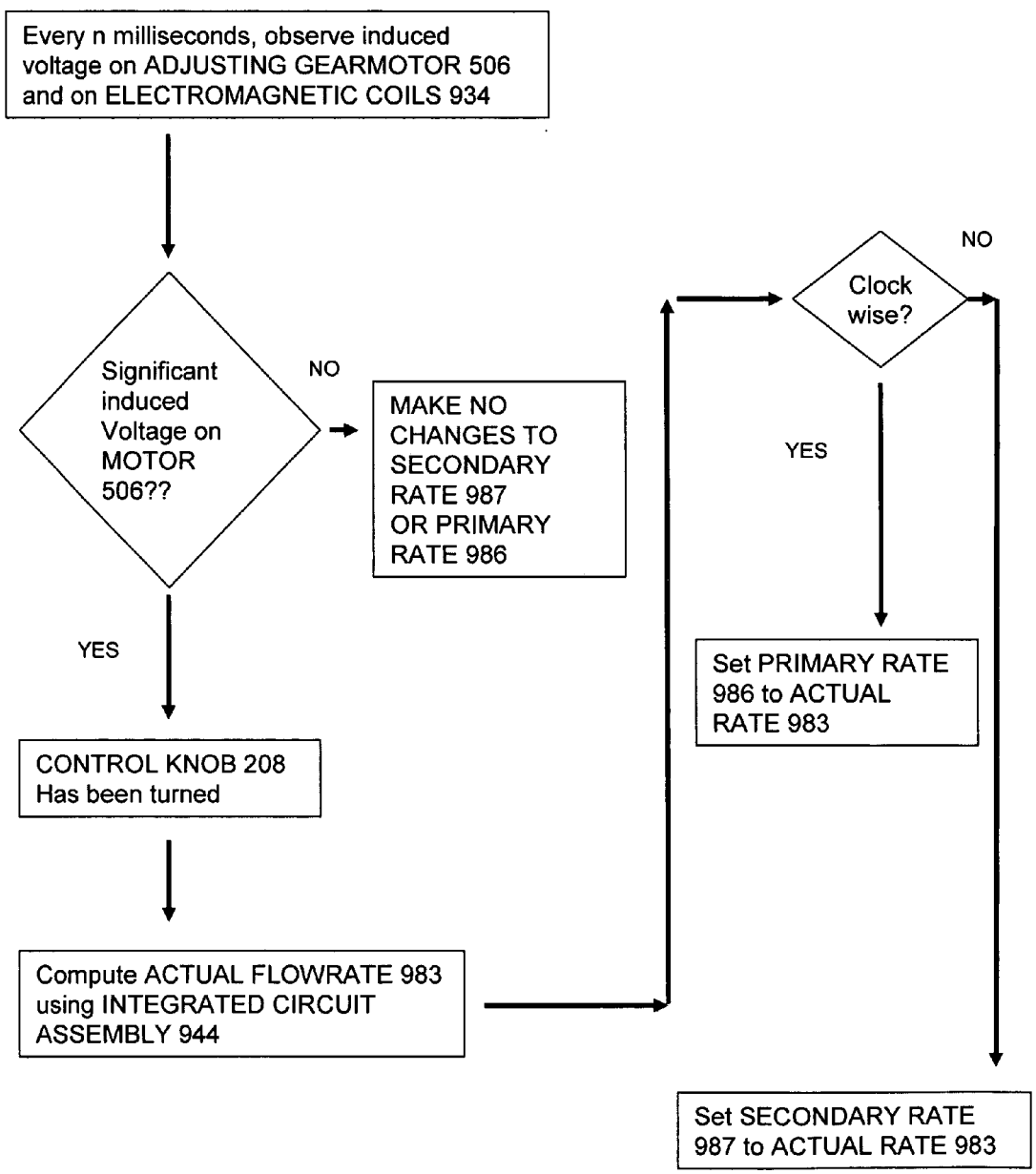
FIG. 24a is a flow chart of the operations that comprise the rate targeting method.

FIG. 24a illustrates the logic of setting flow rate targets for flow originating from either primary inlet line 202 or secondary fluid source connection receptacle 204. First, a determination has been made if resistance control knob 208 has been moved by a user. If movement has occurred, then the most recently computed actual flow rate becomes the new target. This is analogous to the setting of an automotive cruise control target, where the SET button is used to maintain the currently set rate of speed.

Figure 24B:
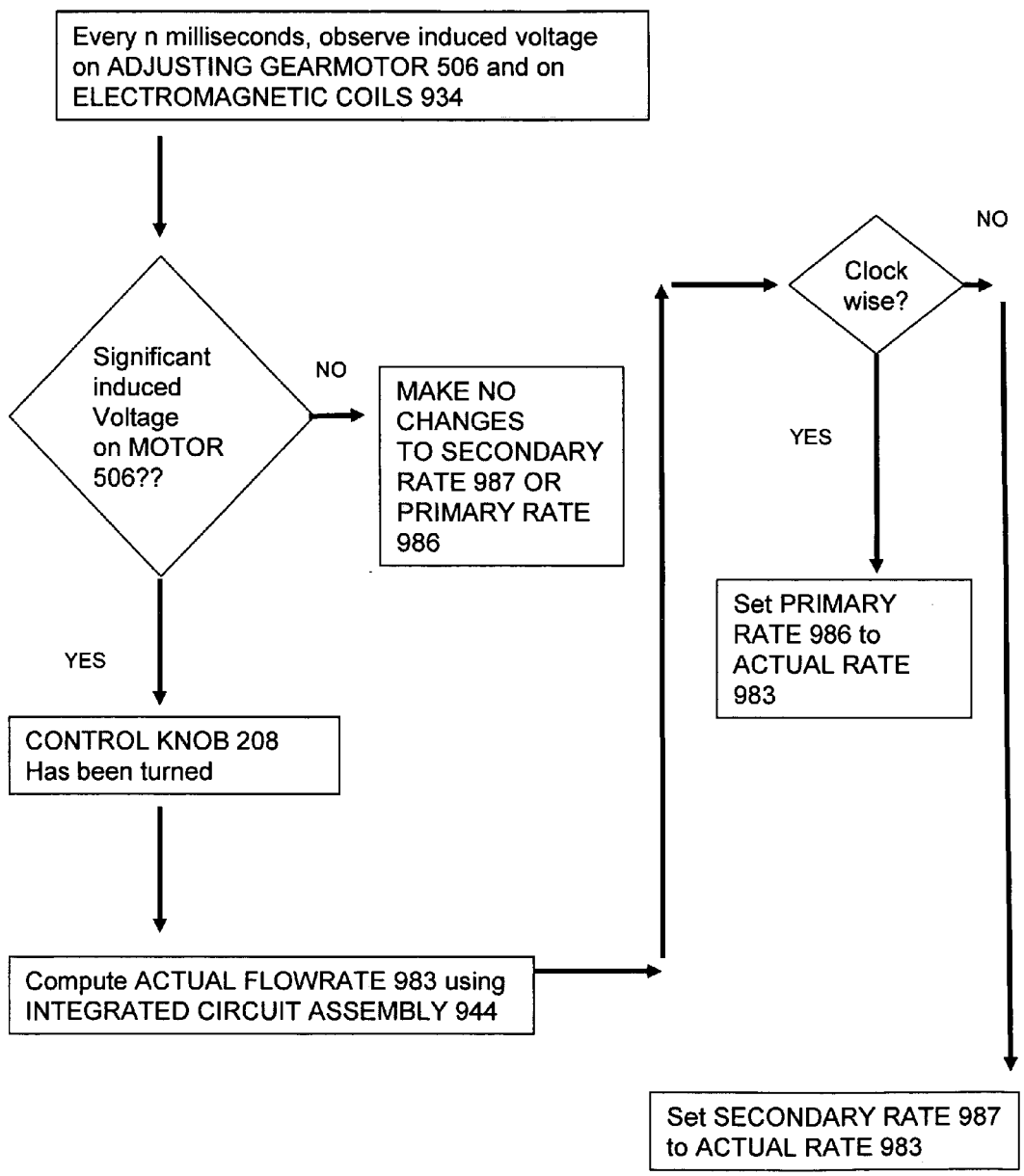
FIG. 24b is a flow chart of the operations that comprise an alternative rate targeting method.

FIG. 24b illustrates alternative logic of setting flow rate targets for flow originating from either primary inlet line 202 or secondary fluid source connection receptacle 204. First, a determination has been made if resistance control knob 208 has been moved by a user. If movement has occurred, then the stored targeted flow rate is incremented or decremented, depending on the direction of rotation of adjusting gear motor 506. The new targeted rate is indicated by graphic display 912 on flow control device 900 (see FIG. 10). Upon release of resistance control knob 208, the control loop continues its normal behavior, as described in FIG. 23, with a new target rate that was set digitally by the user.

While there has been shown and described what is considered to be preferred embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

What is claimed is:

1. A fluid control system, comprising:
   a fluid pathway assembly defining a fluid pathway and having an inline flow sensor element received within said fluid pathway, said sensor element movable in response to a fluid flowing in said fluid pathway;
   a flow control device removably attachable to said fluid pathway assembly and having a sensor for detecting movement of said inline flow sensor element;
   said fluid pathway assembly having a variable flow resistor which is manually adjustable to regulate a rate of fluid flow in the fluid pathway when said flow control device is removed from said fluid pathway assembly;
   a motor attached to the flow control device, said motor operably coupled to said variable flow resistor when said flow control device is attached to said fluid pathway assembly; and
   said variable flow resistor adjustable by said motor under automatic control in response to electronically sensed interactions between said inline flow sensor element and said sensor.

2. The fluid control system of claim 1, further comprising:
   said variable flow resistor further being manually adjustable to regulate a rate of fluid flow in the fluid pathway when said flow control device is attached to said fluid pathway assembly.

3. The fluid control system of claim 1, further comprising:
   said fluid pathway assembly having a first inlet for fluidic coupling to a first fluid source and an outlet for fluidic coupling to a patient; and
   a visual indicator of fluid flow fluidically coupled to said fluid pathway assembly.

4. The fluid control system of claim 3, further comprising:
   said flow control device having a processor for receiving signals from said sensor, the signals representative of movement of said inline flow sensor element; and
   a display on said flow control device for displaying flow rate information in human-viewable form.

5. The fluid control system of claim 4, further comprising:
   said inline flow sensor element including an inline flow impeller rotatably mounted within said flow pathway and a magnet mounted on said inline flow impeller; and
   said sensor including an electromagnetic sensor for generating signals in response to movement of said magnet.

6. The fluid control system of claim 5, further comprising:
   a second inlet for fluidic coupling to a second fluid source; and
   said processor for receiving the signals generated by electromagnetic sensor in response to movement of said magnet and determining whether the fluid flowing in the fluid pathway is from the first fluid source or the second fluid source.

7. The fluid control system of claim 5, further comprising:
   a power supply electrically coupled to said electromagnetic sensor for applying a current to said electromagnetic sensor for generating an electromagnetic field, said magnet and inline flow impeller movable in response to the electromagnetic field.

8. The fluid control system of claim 7, further comprising:
said processor for calculating flow rate information based on one or both of:
   passive movement of said inline flow impeller sensed by said electromagnetic sensor; and
   movement of said inline flow impeller responsive to an electromagnetic field generated by said electromagnetic sensor.

9. The fluid control system of claim 5, further comprising:
said fluid pathway assembly maintaining a stable flow rate when said flow control device is removed from said fluid pathway assembly.

10. The fluid control system of claim 9, further comprising:
said flow control device operable to automatically adjust said variable flow resistor to achieve a first target flow rate if the fluid flowing in the fluid pathway is from the first fluid source and a second target flow rate if the fluid flowing in the fluid pathway is from the second source.

11. A method for controlling a flow of fluid from a fluid source to a patient, said method comprising:
   connecting a first fluid source containing a first fluid to be infused into a patient to a first inlet of a fluid pathway assembly having a manually adjustable variable flow resistor, the fluid pathway assembly defining a fluid pathway and having an inline flow sensor element received within the fluid pathway, the sensor element movable in response to fluid flowing in the fluid pathway;
   providing a fluid control device which is removably attachable to the fluid pathway assembly, the fluid control device having a sensor for detecting movement of the inline flow sensor element;
   calculating an actual flow rate based on sensed movement of the inline flow sensor element; and
   if the fluid control device is attached to the fluid pathway assembly, monitoring the actual flow rate and automatically adjusting the variable flow resistor to achieve a first target flow rate.

12. The method of claim 11, further comprising:
the variable flow resistor being manually adjustable to regulate a rate of fluid flow in the fluid pathway when the flow control device is removed from the fluid pathway assembly.

13. The method of claim 12, further comprising:
providing one or both of a visual indicator of fluid flow for providing a visual indication of flow rate when the flow control device is removed from the fluid pathway assembly and a display on the flow control device for displaying flow rate information in human-viewable form when the flow control device is attached to the fluid pathway assembly.

14. The method of claim 11, further comprising:
the inline flow sensor element including an inline flow impeller rotatably mounted within the flow pathway and a magnet mounted on the inline flow impeller; and
the sensor including an electromagnetic sensor for generating signals in response to movement of the magnet.

15. The method of claim 14, further comprising:
sensing passive movement of the inline flow impeller using the electromagnetic sensor; and
calculating a flow rate based on the sensed passive movement.

16. The method of claim 14, further comprising:
applying a current to the electromagnetic sensor to generate an electromagnetic field; and
sensing movement of the inline flow impeller responsive to the electromagnetic field; and
calculating a flow rate based on the sensed movement.

17. The method of claim 14, further comprising:
connecting a second fluid source containing a second fluid to be infused into a patient to a second inlet of a fluid pathway assembly.

18. The method of claim 17, further comprising:
receiving the signals generated by electromagnetic sensor in response to movement of the magnet;
determining whether the fluid flowing in the fluid pathway is from the first fluid source or the second fluid source.

19. The method of claim 18, further comprising:
adjusting the variable flow resistor to achieve a first target flow rate if the fluid flowing in the fluid pathway is from the first fluid source; and
adjusting the variable flow resistor to achieve a second target flow rate if the fluid flowing in the fluid pathway is from the first second source.

20. A method for controlling a flow of fluid in a fluid flow control system, said method comprising:
   connecting a fluid source to an inlet of a fluid pathway assembly, the fluid pathway assembly defining a fluid pathway and having an inline flow sensor element received within the fluid pathway, the sensor element movable in response to fluid flowing in the fluid pathway;
   providing a fluid control device having a sensor for detecting movement of the inline flow sensor element;
   applying a force to the inline flow sensor element;
   detecting a response of the inline flow sensor element to the force applied to the inline flow sensor element;
   calculating an actual flow rate based on the detected response of the inline flow sensor element to the force applied to the inline flow sensor element.

* * * * *